United States Patent
Xiong et al.

(10) Patent No.: US 7,625,732 B2
(45) Date of Patent: Dec. 1, 2009

(54) ISOLATED DNA ENCODING CULLIN REGULATORS ROC1 AND ROC2, ISOLATED PROTEINS ENCODED BY THE SAME, AND METHODS UTILIZING THE SAME

(75) Inventors: Yue Xiong, Chapel Hill, NC (US); Tomohiko Ohta, Tokyo (JP)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 11/483,907

(22) Filed: Jul. 10, 2006

(65) Prior Publication Data

US 2006/0252098 A1    Nov. 9, 2006

Related U.S. Application Data

(62) Division of application No. 09/541,462, filed on Mar. 31, 2000, now Pat. No. 7,078,203.

(60) Provisional application No. 60/127,261, filed on Mar. 31, 1999, provisional application No. 60/166,927, filed on Nov. 22, 1999.

(51) Int. Cl.
  C12N 9/00    (2006.01)
  C07K 14/00   (2006.01)
  C07H 21/00   (2006.01)
  C12P 21/00   (2006.01)
  C12N 15/00   (2006.01)
  C12N 5/10    (2006.01)
  C12N 1/21    (2006.01)

(52) U.S. Cl. ............ 435/183; 435/69.1; 435/320.1; 435/325; 435/252.3; 530/350; 536/23.2

(58) Field of Classification Search .......... 530/350; 435/320.1, 69.1, 325, 252.3, 183, 69; 536/23.1, 536/23.5, 23.2
See application file for complete search history.

(56) References Cited

U.S. PATENT DOCUMENTS

| | | | | |
|---|---|---|---|---|
| 5,871,973 | A | 2/1999 | Hillman et al. | 435/69.1 |
| 5,922,318 | A | 7/1999 | Bandman et al. | 424/94.1 |
| 5,968,747 | A | 10/1999 | Hillman et al. | 435/6 |
| 5,968,761 | A | 10/1999 | Rolfe et al. | 435/15 |
| 5,968,797 | A | 10/1999 | Ni et al. | 435/193 |
| 6,068,982 | A | 5/2000 | Rolfe et al. | 435/7.21 |
| 6,068,994 | A | 5/2000 | Barr | 435/69.7 |
| 6,783,961 | B1 | 8/2004 | Edwards et al. | |
| 6,858,709 | B1 | 2/2005 | Conaway et al. | |
| 2005/0019813 | A1 | 1/2005 | Conaway et al. | |

FOREIGN PATENT DOCUMENTS

| | | |
|---|---|---|
| EP | 1 033 401 A2 | 9/2000 |
| WO | WO 9932514 | 1/1999 |
| WO | WO 9906554 | 11/1999 |
| WO | 00/50445 | 8/2000 |

OTHER PUBLICATIONS

Branden et al., Introduction to Protein Structure, Garland Publishing Inc., New York, p. 247, 1991.*
Swaroop et al., Oncogene 19:2855-2866, 2000.*
Duan et al., Molecular and Cellular Biology 19(4):3145-3155, Apr. 1999.*
Duan et al., "SAG, a Novel Zinc RING Finger Protein that Protects Cells from Apoptosis Induced by Redox Reagents", *Molecular and Cellular Biology* 19: 3145-3155 (Apr. 1999).
International Search Report, Nov. 6, 2000, for Application No. PCT/US00/08592.
Brown, D. et al. *Pip1p, a new subunit of the SCF-Pop ubiquitin ligase complex in S. pombe.* Accession No. O13959. Jun. 1, 1998. Database on-line. Available from EMBL.
Brown, D. et al. *S.pombe chromosome 1 cosmid c23H4.* Accession No. Z98977. Sep. 8, 1997. Database on-line. Available from EMBL.
Fujiwara, T. et al. *Human fetal brain cDNA 5'-end GEN-090E07.* Accession No. D52876. Aug. 24, 1995. Database on-line. Available from EMBL.
Hangjun, D. et al. SAG, a novel zinc RING finger protein that protects cells from apoptosis induced by redox agents, *Molecular and Cellular Biology*. 19:3145-3155 (1999).
Hillier et al. *The WashU-Mrck EST Project.* Accession No. W38711. May 17, 1996. Database on-line. Available from EMBL.
Ohta, T. et al. ROC1, a homolog of APC11, represents a family of cullin partners with an associated ubiquitin ligase activity, *Molecular Cell.* 3:535-541 (1999).
Skowyra, D. et al. Reconstitution of $G_1$ Cyclin Ubiquitination with Complexes Containing $SCF^{Grr1}$ and Rbx1 , *Science.* 284:662-665 (1999).
Tanimura, S. et al. MDM2 interacts with MDMX through their RING finger domains, *FEBS Letters.* 447:5-9 (1999).

(Continued)

Primary Examiner—Delia M Ramirez
(74) Attorney, Agent, or Firm—Myers Bigel Sibley & Sajovec, P.A.

(57) ABSTRACT

The present invention provides isolated polynucleotide sequences encoding the proteins ROC1 and ROC2, the isolated proteins themselves, expression vectors containing at least a fragment of the ROC1 and ROC2 polynucleotide sequences, and host cells comprising the same. Methods of producing the ROC1 and ROC2 proteins are also disclosed, and methods of detecting the polynucleotides in samples are included in this invention, as are antibodies to the ROC1 and ROC2 proteins and antisense molecules complementary to polynucleotides encoding the same. The present invention further includes methods for screening bioactive agents that are capable of binding to a ROC protein, methods of screening bioactive agents capable of interfering with the binding of ROC proteins, and methods of screening bioactive agents capable of modulating the activity of a ROC protein. Such screening methods are capable of identifying compounds that have pharmacological. Pharmaceutical formulations comprising such pharmacologically active compounds and methods of administering the same are an additional aspect of this invention.

2 Claims, 15 Drawing Sheets

OTHER PUBLICATIONS

O. Cohen-Fix et al.; Anaphase initiation in *Saccharomyces cerevisiae* is controlled by the APC-dependent degration of the anaphase inhibitor Pdslp; *Genes & Dev.* 10:3081-3093 (1996).

A. Hershko; Roles of ubiquitin-mediated proteolysis in cell cycle control; *Curr. Opin. Cell. Biol.* 9:788-799 (1997).

M. Brandeis et al.; The proteolysis of mitotic cyclins in mammalian cells persists from the end of mitosis until the onset of S phase; *EMBO J.* 15:5280-5289 (1996).

N. Mathias et al.; Cdc53p Acts in Concert with Cdc4p and Cdc34p To Control the $G_1$-to-S-Phase Transition and Identifies a Conserved Family of Proteins; *Mol. Cell. Biol.* 16:6634-6643 (1996).

K. M. Lonergan et al.; Regulation of Hypoxia-Inducible mRNAs by the von Hippel-Lindau Tumor Suppressor Protein Requires Binding to Complexes Containing Elongins B/C and Cul2; *Mol. Cell. Biol* 18:732-741 (1998).

L-C Chen et al.; The Human Homologue for the *Caenorhabditis elegans* cul-4 Gene is Amplified and Overexpressed in Primary Breast Cancers; *Cancer Res.* 58:3677-3683 (1998).

J. Michel et al.; Human CUL-1, but not Other Cullin Family Members, Selectively Interacts with SKP1 to Form a Complex with SKP2 and Cyclin A; *Cell Growth Differ.* 9:435-449 (1998).

M. Scheffner et al.; Protein ubiquitination involving an E-1-E2-E3 enzyme ubiquitin thioester cascade; *Nature* 373:81-83 (1995).

C. Michaelis et al.; Cohesins: Chromosomal Proteins that Prevent Premature Separation of Sister Chromatids; *Cell* 91:35-45 (1997).

R.M.R. Feldman et al.; A Complex of Cdc4p, Skp1p, and Cdc53p/Cullin Catalyzes Ubiquitination of the Phosphorylated CDK Inhibitor Sic1p; *Cell* 91:221-230 (1997).

C. Bai et al.; SKP1 Connects Cell Cycle Regulators to the Ubiquitin Proteolysis Machinery through a Novel Motif, the F-Box; *Cell* 86:263-274 (1996).

A. R. Willems et al.; Cdc53 Targets Phosphorylated G1 Cyclins for Degradation by the Ubiquitin Proteolytic Pathway; *Cell* 86:453-463 (1996).

D. Skowyra et al.; F-Box Proteins Are Receptors that Recruit Phosphorylated Substrates to the SCF Ubiquitin-Ligase Complex; *Cell* 91:209-219 (1997).

E. T. Kipreos et al.; cul-1 Is Required for Cell Cycle Exit in *C. elegans* and Identifies a Novel Gene Family; *Cell* 85:829-839 (1996).

A. Amon et al.; Closing the Cell Cycle Circle in Yeast: G2 Cyclin Proteolysis Initiated at Mitosis Persists until the Activation of G1 Cyclins in the Next Cycle; *Cell* 77:1037-1050 (1994).

M. Schwab et al.; Yeast Hct1 Is a Regulator of C1b2 Cyclin Proteolysis; *Cell* 90:683-693 (1997).

S. J. Sigrist et al.; *Drosophila* fizzy-related Down-Regulates Mitotic Cyclins and is Required for Cell Proliferation Arrest and Entry into Endocycles; *Cell* 90:671-681 (1997).

M. Scheffner et al.; The HPV-16 E6 and E6-AP Complex Functions as a Ubiquitin-Protein Ligase in the Ubiquitination of p53; *Cell* 75:495-505 (1993).

H. Funabiki et al.; Cut2 proteolysis required for sister-chromatid separation in fission yeast; *Nature* 381:438-441 (1996).

M. Glotzer et al.; Cyclin is degraded by the ubiquitin pathway; *Nature* 349:132-138 (1991).

R. W. King et al.; How Proteolysis Drives the Cell Cycle; *Science* 274:1652-1659 (1996).

J-M. Peters et al.; Identification of BIME as a Subunit of the Anaphase-Promoting Complex; *Science* 274:1199-1201 (1996).

Z-K Yu et al.; Human CUL-1 associates with the SKP1/SKP2 complex and regulates $p21^{C1P1/WAF1}$ and cyclin D proteins; *Proc. Natl. Acad. Sci. USA* 95:11324-11329 (1998).

S. A. Lyapina et al.; Human CUL1 forms an evolutionarily conserved ubiquitin ligase complex (SCF) with SKP1 and an F-box protein, *Proc. Natl Acad. Sci. USA* 95:7451-7456 (1998).

S. Lahav-Baratz et al.; Reversible phosphorylation controls the activiy of cyclosome-associated cyclin-ubiquitin ligase; *Proc. Natl Acad. Sci. USA* 92:9303-9307 (1995).

Y-L Juang e al.; APC-Mediated Proteolysis of Asel and the Morphogenesis of the Mitotic Spindle; *Science* 275:1311-1314 (1997).

R. Visintin et al; CDC20 and CDH1: A Family of Substrate-Specific Activators of APC-Dependent Proteolysis; *Science* 278:460-463 (1997).

R. Verma et al.; Phosphorylatin of Sic1p by $G_1$ Cdk Required for its Degradation and Entry into S Phase; *Science* 278:455-460 (1997).

H. Yu et al.; Identification of a Cullin Homology Region in a Subunit of the Anaphase-Promoting Complex; *Science* 279:1219-1222 (1998).

W. Zachariae et al.; Mass Spectrometric Analysis of the Anaphase-Promoting Complex from Yeast: Identification of a Subunit Related to Cullins; *Science* 279:1216-1219 (1998).

J. M. Huibregtse et al.; A family of proteins structurally and functionally related to the E6-AP ubiquitin-protein ligase; *Proc. Natl. Acad. Sci. USA* 92:2563-2567 (1995).

A. Varshavsky; The N-end rule: Functions, mysteries, uses; *Proc. Natl. Acad. Sci. USA* 93:12142-12149 (1996).

J. Lisztwan et al.; Association of human CUL-1 and ubiquitin-conjugating enzyme CDC34 with the F-box protein $p45^{SKP2}$: evidence for evolutionary conservation in the subunit composition of the CDC34-SCF pathway; *The EMBO J.* 17, No. 2:368-383 (1998).

A. Pause et al.; The von Hippel-Lindau tumor-suppressor gene product forms a stable complex with human CUL-2, a member of the Cdc53 family of proteins; *Proc. Natl. Acad. Sci. USA* 94:2156-2161 (1997).

F. Ning Li et al.; Grr1 of *Saccharomyces cerevisiae* is connected to the ubiquitin proteolysis machinery through Skp1: coupling glucose sensing to gene expression and the cell cycle; *The EMBO J.* 16, No. 18:5629-5638 (1997).

M. Hochstrasser; Ubiquitin-Dependent Protein Degradation; *Annu. Rev. Genet.* 30:405-439 (1996).

P. Kaiser et al.; Cdc34 and the F-box protein Met30 are required for degradation of the Cdk-inhibitory kinase Swe1; *Genes & Dev.* 12:2587-2597 (1998).

G. Fang et al.; Direct Binding of CDC20 Protein Family Members Activates the Anaphase-Promoting Complex in Mitosis and G; *Molecular Cell* 2:163-171.

H. Yu; Identification of a novel ubiquitin-conjugating enzyme involved in mitotic cyclin degradation; *Current Biology* 6, No. 4:455-466.

Arino et al., GenBank accession No. CAA99155, Aug. 1997.

Bork, *Genome Research* 10:398-400 (2000).

Broun et al. *Science* 282: 1315-1317 (1998).

Kamura et al., *Science* 284: 657-661 (Apr. 1999).

Okresz, GenEMBL accession No. AY052401 (2001).

Seffernick et al. *J. Bacteriol.* 183: 2405-2410 (2001).

Van de Loo et al. *Proc. Natl. Acad. Sci.* 92: 6743-6747 (1995).

Witkowski et al., *Biochemistry* 38: 11643-11650 (1999).

Database EMBL [Online]; "*Homo sapiens* Full Length Insert cDNA Clone YQ60A05" Retrieved from EBI Accession No. EMBL: AF085906 (Sep. 3, 1998)(2 pages).

Database EMBL [Online]; "*Homo sapiens* Ring-box Protein 1 (RBX1) mRNA, Complete cds" Retrieved from EBI Accession No. EMBL: AF140598 (May 11, 1999)(2 pages).

European Search Report for European Application No. 07023230.1 dated Oct. 1, 2008 (5 pages).

* cited by examiner

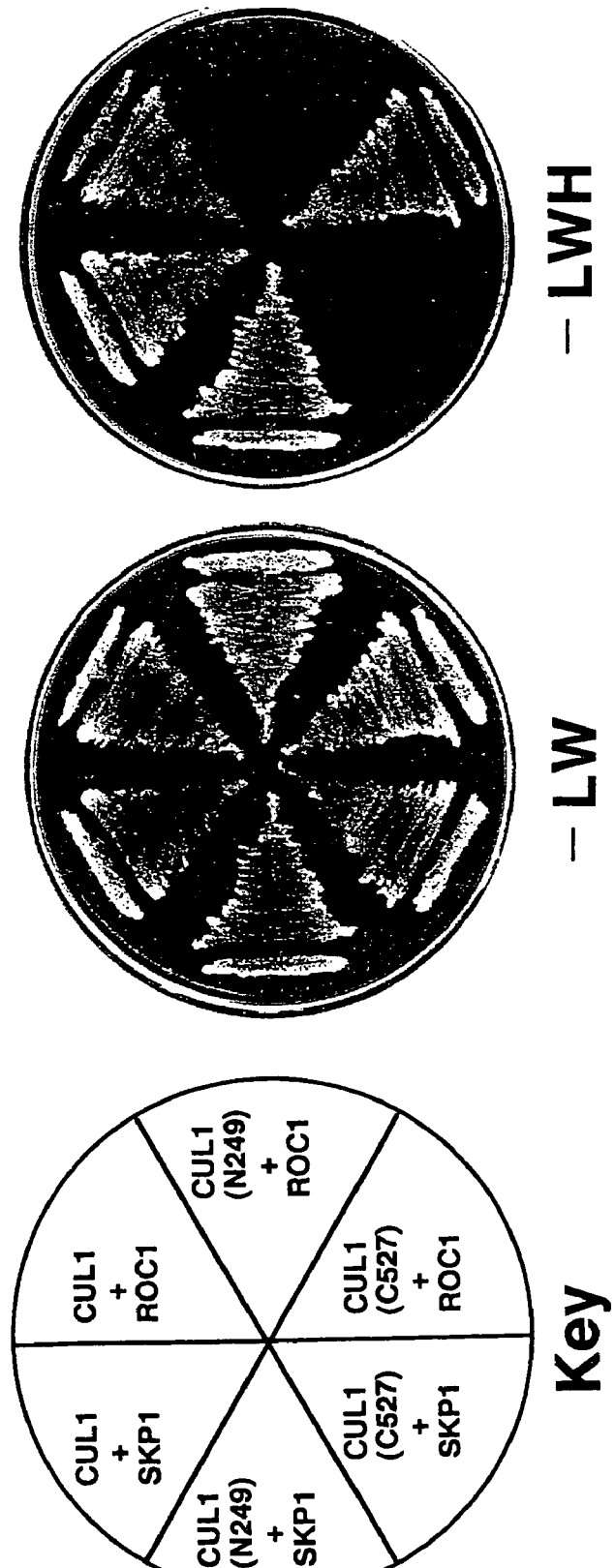
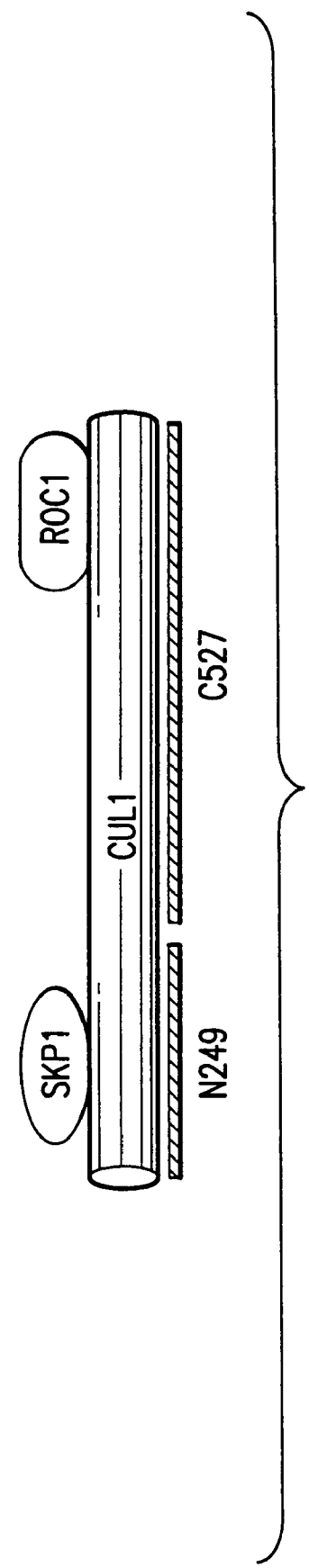
FIG. 1B

ROC1

```
ATGGCGGCGGCAGCGGATGGATCTGGATACCCCGAGCCGGCCGGGCCGCAAGAGCGCTTTGAAGTGAAAAAGTGAATGCAGTA  90
 M  A  A  A  M  D  V  D  T  P  S  G  T  N  S  G  A  G  K  K  R  F  E  V  K  K  W  N  A  V   30
GCCCTTCTGGCTGGCTGGGATATTGTGGTTGATAACTGTGCCATCTGCAGGAACCACATTATGGATCTTTGCATAGAATGTCAAGCTAACCAG 180
 A  L  W  A  M  D  I  V  V  D  N  C  A  I  C  R  N  H  I  M  D  L  C  I  E  C  Q  A  N  Q   60
GCGTCCGCTACTTCAGAAGAGTGTACTGTCGCATGGGAGTCTGTAACCATGCTTTTCACTTCCACTGATGATAATGAGTGCGTGGCTGCCAAAACA 270
 A  S  A  T  S  E  E  C  T  V  A  W  G  V  C  N  H  I  A  F  H  F  H  C  I  S  R  W  L  K  T   90
CGACAGGTGTGTCCATTGGACAACAGAGAGTGGGAATTCCAAAAGTATGGGCACTAG 327
 R  Q  V  C  P  L  D  N  R  E  W  E  F  Q  K  Y  G  H  *  108
```

FIG. 2A

```
ROC1-Hs   22 FEVKKWNAVALMAMDIVVDNCAICRNHIMDLCIECQANQASATSEECTVAWGVCNHAFHFHCISRWL----KTRQVC PLDNREWEF 108
ROC1-Dm   22 FEVKKWNAVALMAMDIVVDNCAICRNHIMDLCIECQANQASATSEECTVAWGVCNHAFHFHCISRWL----KTRQVC PLDNREYDF 108
ROC1-Ce   24 FEVKKWSAVALMAMDIQVDNCAICRNHIMDLCIECQANQAAGLKDRCTVAWGNCNHAFHFHCISRWL----KTRQVC PLDNREWEF 110
ROC1-At   32 FEIKKWNSAVALMAMDIVVDNCAICRNHIMDLCIECQANQASATSEECTVAWGVCNHAFHFHCISRWL----KTRQVC PLDNSEWEF 118
ROC1-Sp   21 FEIKKWNAVALMQWDIVVDNCAICRNHIMDLCIECQANTDSAAAQECTVAWGTCNHAFHFHCISRWL----NTRNVC PLDNREWEF 113
ROC1-Sc   35 FEIKKWTAVAFWSMDLAVDNCAICRNHIMFPCIECQPFKAMTDTDNECVAAWGVCNHIAFHLHCINKWI---KTRIDAC PLDNQPWQL 121
ROC2-Hs    2 FSLKKWNAVAMWSMDVECDTCAICRVQVNDACLRCQAEN---KQEDCVVVWGECNHSFHNCCMSLMV---KQNNRC PLCQQDWVV  85
ROC2-Ce   30 FVLKKWNALAVWAMWDVECDTCAICRVHLMEECLRCQSEP---SAE-CYVVWGDCNHISFHHCMTQWI--RQNNRC PLCQKDWVV 112
APC11-Hs   3 VKIKCWNGVATWLMVANDENCGICRMAFNGCCPDCKVPG-------DDCPLVWGQCSHCFHMHCILKWLHAQQVQQHC PMCRQEWKF  84
APC11-Dm   3 VTIKSWTGVATWRWIANDENCGICRMSFESTCPECALPG-------DDCPLVWGVCSHCFHMHCIVKWLNLQPLNKQC PMCRQSWKF  85
APC11-Ce  51 TTVKKLHVCGEWKWL[3]DTCGICRHAFHRHCIDKWI[5]QPRAQC PLCHQDWTI 135
APC11-Sc   3 VKIMEVHSVFAWSM[21]DVCGICHASYNGTCPSCKFPG-------DQCPLVTGLCHHNFHDHCIYRWLDTPTSKGLC PMCRQTFQL 165
```

FIG. 2B

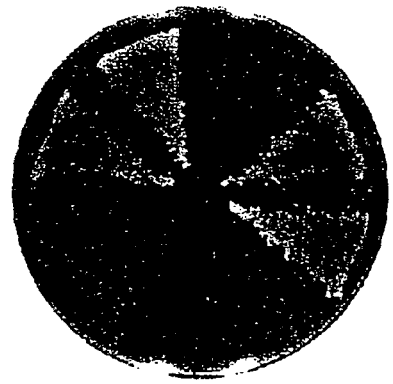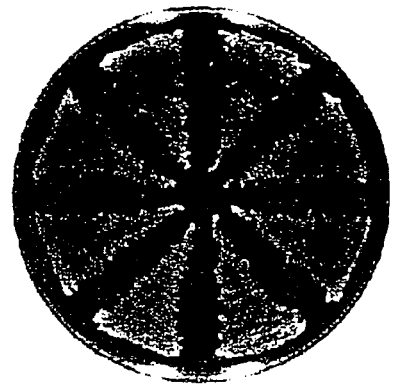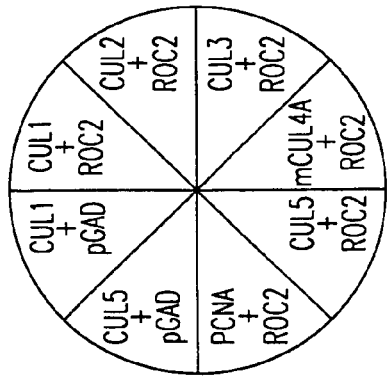
FIG. 4A
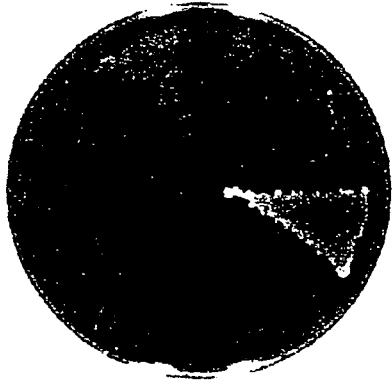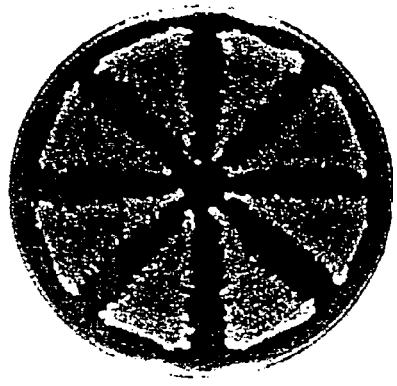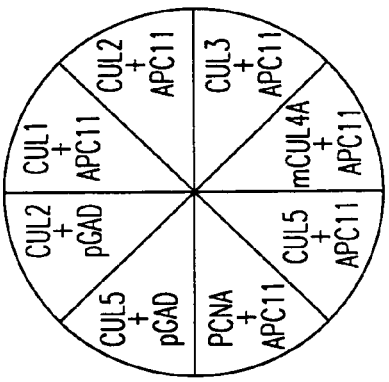
FIG. 4B

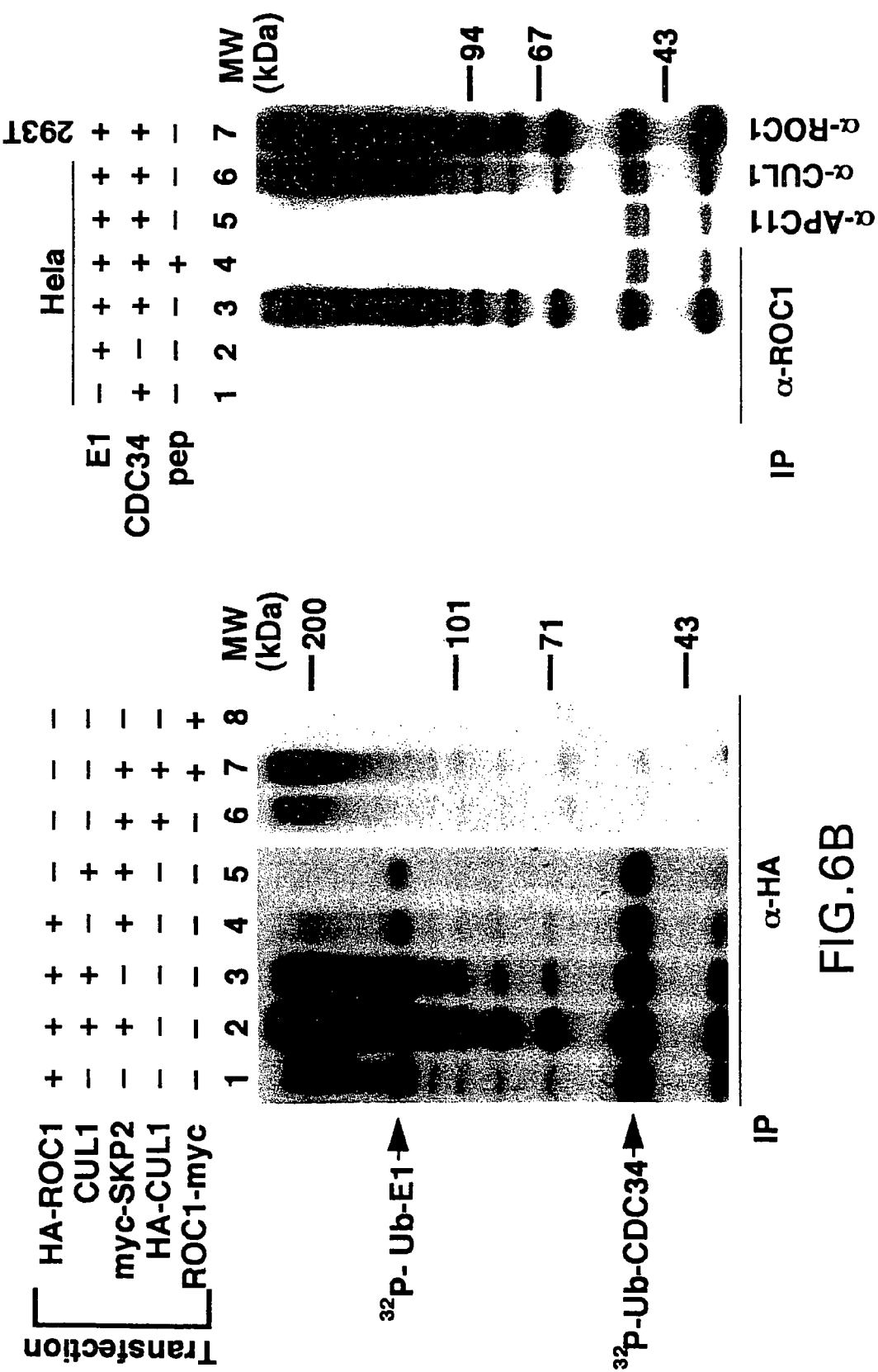

SEQUENCE LISTING

<160> NUMBER OF SEQ ID NOS: 41

<210> SEQ ID NO 1
<211> LENGTH: 327
<212> TYPE: DNA
<213> ORGANISM: Homo sapiens
<220> FEATURE:
<221> NAME/KEY: CDS
<222> LOCATION: (1)..(324)
<223> OTHER INFORMATION:

<400> SEQUENCE: 1

```
atg gcg gca gcg atg gat gtg gat acc ccg agc ggc acc aac agc ggc        48
Met Ala Ala Ala Met Asp Val Asp Thr Pro Ser Gly Thr Asn Ser Gly
1               5                   10                  15 gcg ggc aag aag cgc ttt gaa gtg aaa aag tgg aat gca gta gcc ctc        96
Ala Gly Lys Lys Arg Phe Glu Val Lys Lys Trp Asn Ala Val Ala Leu
            20                  25                  30 tgg gcc tgg gat att gtg gtt gat aac tgt gcc atc tgc agg aac cac       144
Trp Ala Trp Asp Ile Val Val Asp Asn Cys Ala Ile Cys Arg Asn His
        35                  40                  45 att atg gat ctt tgc ata gaa tgt caa gct aac cag gcg tcc gct act       192
Ile Met Asp Leu Cys Ile Glu Cys Gln Ala Asn Gln Ala Ser Ala Thr
    50                  55                  60 tca gaa gag tgt act gtc gca tgg gga gtc tgt aac cat gct ttt cac       240
Ser Glu Glu Cys Thr Val Ala Trp Gly Val Cys Asn His Ala Phe His
65                  70                  75                  80 ttc cac tgc atc tct cgc tgg ctc aaa aca cga cag gtg tgt cca ttg       288
Phe His Cys Ile Ser Arg Trp Leu Lys Thr Arg Gln Val Cys Pro Leu
                85                  90                  95 gac aac aga gag tgg gaa ttc caa aag tat ggg cac tag                   327
Asp Asn Arg Glu Trp Glu Phe Gln Lys Tyr Gly His
            100                 105
```

<210> SEQ ID NO 2
<211> LENGTH: 108
<212> TYPE: PRT
<213> ORGANISM: Homo sapiens

<400> SEQUENCE: 2

```
Met Ala Ala Ala Met Asp Val Asp Thr Pro Ser Gly Thr Asn Ser Gly
1               5                   10                  15

Ala Gly Lys Lys Arg Phe Glu Val Lys Lys Trp Asn Ala Val Ala Leu
            20                  25                  30

Trp Ala Trp Asp Ile Val Val Asp Asn Cys Ala Ile Cys Arg Asn His
        35                  40                  45

Ile Met Asp Leu Cys Ile Glu Cys Gln Ala Asn Gln Ala Ser Ala Thr
    50                  55                  60

Ser Glu Glu Cys Thr Val Ala Trp Gly Val Cys Asn His Ala Phe His
65                  70                  75                  80

Phe His Cys Ile Ser Arg Trp Leu Lys Thr Arg Gln Val Cys Pro Leu
                85                  90                  95

Asp Asn Arg Glu Trp Glu Phe Gln Lys Tyr Gly His
            100                 105
```

<210> SEQ ID NO 3
<211> LENGTH: 342
<212> TYPE: DNA
<213> ORGANISM: Homo sapiens
<220> FEATURE:

```
<221> NAME/KEY: CDS
<222> LOCATION: (1)..(339)
<223> OTHER INFORMATION:

<400> SEQUENCE: 3 atg gcc gac gtg gaa gac gga gag gaa acc tgc gcc ctg gcc tct cac      48
Met Ala Asp Val Glu Asp Gly Glu Glu Thr Cys Ala Leu Ala Ser His
1               5                   10                  15 tcc ggg agc tca ggc tca acg tcg gga ggc gac aag atg ttc tcc ctc      96
Ser Gly Ser Ser Gly Ser Thr Ser Gly Gly Asp Lys Met Phe Ser Leu
            20                  25                  30 aag aag tgg aac ccg gtg gcc atg tgg agc tgg gac gtg gag tgc gat     144
Lys Lys Trp Asn Pro Val Ala Met Trp Ser Trp Asp Val Glu Cys Asp
        35                  40                  45 acg tgc gcc atc tgc agg gtc cag gtg atg gat gcc tgt ctt aga tgt     192
Thr Cys Ala Ile Cys Arg Val Gln Val Met Asp Ala Cys Leu Arg Cys
    50                  55                  60 caa gct gaa aac aaa caa gag gac tgt gtt gtg gtc tgg gga gaa tgt     240
Gln Ala Glu Asn Lys Gln Glu Asp Cys Val Val Val Trp Gly Glu Cys
65                  70                  75                  80 aat cat tcc ttc cac aac tgc tgc atg tcc ctg tgg gtg aaa cag aac     288
Asn His Ser Phe His Asn Cys Cys Met Ser Leu Trp Val Lys Gln Asn
                85                  90                  95 aat cgc tgc cct ctc tgc cag cag gac tgg gtg gtc caa aga atc ggc     336
Asn Arg Cys Pro Leu Cys Gln Gln Asp Trp Val Val Gln Arg Ile Gly
            100                 105                 110 aaa tga                                                              342
Lys

<210> SEQ ID NO 4
<211> LENGTH: 113
<212> TYPE: PRT
<213> ORGANISM: Homo sapiens

<400> SEQUENCE: 4

Met Ala Asp Val Glu Asp Gly Glu Glu Thr Cys Ala Leu Ala Ser His
1               5                   10                  15

Ser Gly Ser Ser Gly Ser Thr Ser Gly Gly Asp Lys Met Phe Ser Leu
            20                  25                  30

Lys Lys Trp Asn Pro Val Ala Met Trp Ser Trp Asp Val Glu Cys Asp
        35                  40                  45

Thr Cys Ala Ile Cys Arg Val Gln Val Met Asp Ala Cys Leu Arg Cys
    50                  55                  60

Gln Ala Glu Asn Lys Gln Glu Asp Cys Val Val Val Trp Gly Glu Cys
65                  70                  75                  80

Asn His Ser Phe His Asn Cys Cys Met Ser Leu Trp Val Lys Gln Asn
                85                  90                  95

Asn Arg Cys Pro Leu Cys Gln Gln Asp Trp Val Val Gln Arg Ile Gly
            100                 105                 110

Lys

<210> SEQ ID NO 5
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 5
tttaaagaga aataggatcc catgagcaac gaa                                  33
```

```
<210> SEQ ID NO 6
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 6
ttaaatgttt acggggaatt cattttttca cct                                    33

<210> SEQ ID NO 7
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 7
ggcaatacag attaggatcc tatgaaagtt aaa                                    33

<210> SEQ ID NO 8
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 8
aattgtgatt tctagaattc tttttttatcg taa                                   33

<210> SEQ ID NO 9
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 9
atccccatgg ctatgataac taataagaaa ata                                    33

<210> SEQ ID NO 10
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 10
ctgcagagct cgttaggaaa ggtaatggta ata                                    33

<210> SEQ ID NO 11
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 11
atccccatgg ctatgataaa tgagagcgtt tcc                                    33

<210> SEQ ID NO 12
<211> LENGTH: 33
<212> TYPE: DNA
<213> ORGANISM: Artificial sequence
<220> FEATURE:
```

<223> OTHER INFORMATION: Synthetic oligonucleotide primer

<400> SEQUENCE: 12
agctcgtcga cattagtact tgtaagttgc tat                         33

<210> SEQ ID NO 13
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 13
atccccatgg ctatgtcatt tcagattacc cca                         33

<210> SEQ ID NO 14
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 14
agctcgtcga catcatgagt ttttatgccc att                         33

<210> SEQ ID NO 15
<211> LENGTH: 15
<212> TYPE: PRT
<213> ORGANISM: Artificial sequence
<220> FEATURE:
<223> OTHER INFORMATION: Synthetic peptide

<400> SEQUENCE: 15

Cys Met Ala Ala Ala Met Asp Val Asp Thr Pro Ser Gly Thr Asn
1               5                   10                  15

<210> SEQ ID NO 16
<211> LENGTH: 13
<212> TYPE: PRT
<213> ORGANISM: Artificial sequence
<220> FEATURE:
<223> OTHER INFORMATION: Synthetic peptide

<400> SEQUENCE: 16

Cys Asp Asn Arg Glu Trp Glu Phe Gln Lys Tyr Gly His
1               5                   10

<210> SEQ ID NO 17
<211> LENGTH: 9
<212> TYPE: PRT
<213> ORGANISM: Artificial sequence
<220> FEATURE:
<223> OTHER INFORMATION: Synthetic peptide

<400> SEQUENCE: 17

Cys Arg Gln Glu Trp Lys Phe Lys Glu
1               5

<210> SEQ ID NO 18
<211> LENGTH: 14
<212> TYPE: PRT
<213> ORGANISM: Artificial sequence
<220> FEATURE:
<223> OTHER INFORMATION: Synthetic peptide

<400> SEQUENCE: 18

Cys Arg Ser Gln Ala Ser Ala Asp Glu Tyr Ser Tyr Val Ala
1               5                   10

<210> SEQ ID NO 19
<211> LENGTH: 60
<212> TYPE: DNA
<213> ORGANISM: Artificial sequence
<220> FEATURE:
<223> OTHER INFORMATION: Synthetic oligonucleotide primer

<400> SEQUENCE: 19
ttctccagtg gcagagaact ttaaagagaa atagttcaac cggatccccg ggttaattaa    60

<210> SEQ ID NO 20
<211> LENGTH: 60
<212> TYPE: DNA
<213> ORGANISM: Artificial sequence
<220> FEATURE:
<223> OTHER INFORMATION: Synthetic oligonucleotide primer

<400> SEQUENCE: 20
acctcggtat gatttaaatg tttacgggca attcattttt gaattcgagc tcgtttaaac    60

<210> SEQ ID NO 21
<211> LENGTH: 60
<212> TYPE: DNA
<213> ORGANISM: Artificial sequence
<220> FEATURE:
<223> OTHER INFORMATION: Synthetic oligonucleotide primer

<400> SEQUENCE: 21
atagacgtat gggcttcaat atgtgcaatg ttggttgcta gaattcgagc tcgtttaaac    60

<210> SEQ ID NO 22
<211> LENGTH: 60
<212> TYPE: DNA
<213> ORGANISM: Artificial sequence
<220> FEATURE:
<223> OTHER INFORMATION: Synthetic oligonucleotide primer

<400> SEQUENCE: 22
catcttcatc aacatccatc ctgtcaactt cgttgctcat gcactgagca gcgtaatctg    60

<210> SEQ ID NO 23
<211> LENGTH: 60
<212> TYPE: DNA
<213> ORGANISM: Artificial sequence
<220> FEATURE:
<223> OTHER INFORMATION: Synthetic oligonucleotide primer

<400> SEQUENCE: 23
caagccaaag gcattgtttc aatctaggga tcaagagcat cggatccccg ggttaattaa    60

<210> SEQ ID NO 24
<211> LENGTH: 60
<212> TYPE: DNA
<213> ORGANISM: Artificial sequence
<220> FEATURE:
<223> OTHER INFORMATION: Synthetic oligonucleotide primer

<400> SEQUENCE: 24
taaaatataa tcgttccaga aacttttttt tttcatttct gaattcgagc tcgtttaaac    60

<210> SEQ ID NO 25
<211> LENGTH: 6
<212> TYPE: PRT

```
<213> ORGANISM: Homo sapiens
<220> FEATURE:
<221> NAME/KEY: PEPTIDE
<222> LOCATION: (1)..(6)
<223> OTHER INFORMATION: Partial protein sequence

<400> SEQUENCE: 25

Lys Asp Val Phe Gln Lys
1               5

<210> SEQ ID NO 26
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Partial protein sequence

<400> SEQUENCE: 26

Lys Ile Phe Leu Glu Asn His Val Arg His Leu His
1               5                   10

<210> SEQ ID NO 27
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: Partial protein sequence

<400> SEQUENCE: 27

Lys Asp Val Phe Glu Arg Tyr Tyr
1               5

<210> SEQ ID NO 28
<211> LENGTH: 7
<212> TYPE: PRT
<213> ORGANISM: Homo sapiens
<220> FEATURE:
<221> NAME/KEY: PEPTIDE
<222> LOCATION: (1)..(7)
<223> OTHER INFORMATION: Partial protein sequence

<400> SEQUENCE: 28

Lys Val Tyr Thr Tyr Val Ala
1               5

<210> SEQ ID NO 29
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Partial protein sequence

<400> SEQUENCE: 29

Lys Arg Ile Glu Ser Leu Ile Asp Arg Asp Tyr
1               5                   10

<210> SEQ ID NO 30
<211> LENGTH: 82
<212> TYPE: PRT
<213> ORGANISM: Homo sapiens
<220> FEATURE:
<221> NAME/KEY: SIMILAR
<222> LOCATION: (1)..(82)
```

<223> OTHER INFORMATION: Partial protein sequence

<400> SEQUENCE: 30

```
Phe Glu Val Lys Lys Trp Asn Ala Val Ala Leu Trp Ala Trp Asp Ile
1               5                   10                  15
Val Val Asp Asn Cys Ala Ile Cys Arg Asn His Ile Met Asp Leu Cys
                20                  25                  30
Ile Glu Cys Gln Ala Asn Gln Ala Ser Ala Thr Ser Glu Glu Cys Thr
            35                  40                  45
Val Ala Trp Gly Val Cys Asn His Ala Phe His Phe His Cys Ile Ser
        50                  55                  60
Arg Trp Leu Lys Thr Arg Gln Val Cys Pro Leu Asp Asn Arg Glu Trp
65                  70                  75                  80
Glu Phe
```

<210> SEQ ID NO 31
<211> LENGTH: 82
<212> TYPE: PRT
<213> ORGANISM: Drosophila melanogaster
<220> FEATURE:
<221> NAME/KEY: SIMILAR
<222> LOCATION: (1)..(82)
<223> OTHER INFORMATION: Partial protein sequence

<400> SEQUENCE: 31

```
Phe Glu Val Lys Lys Trp Asn Ala Val Ala Leu Trp Ala Trp Asp Ile
1               5                   10                  15
Val Val Asp Asn Cys Ala Ile Cys Arg Asn His Ile Met Asp Leu Cys
                20                  25                  30
Ile Glu Cys Gln Ala Asn Gln Ala Ser Ala Thr Ser Glu Glu Cys Thr
            35                  40                  45
Val Ala Trp Gly Val Cys Asn His Ala Phe His Phe His Cys Ile Ser
        50                  55                  60
Arg Trp Leu Lys Thr Arg Gln Val Cys Pro Leu Asp Asn Arg Glu Tyr
65                  70                  75                  80
Asp Phe
```

<210> SEQ ID NO 32
<211> LENGTH: 82
<212> TYPE: PRT
<213> ORGANISM: Caenorhabditis elegans
<220> FEATURE:
<221> NAME/KEY: SIMILAR
<222> LOCATION: (1)..(82)
<223> OTHER INFORMATION: Partial protein sequence

<400> SEQUENCE: 32

```
Phe Glu Val Lys Lys Trp Ser Ala Val Ala Leu Trp Ala Trp Asp Ile
1               5                   10                  15
Gln Val Asp Asn Cys Ala Ile Cys Arg Asn His Ile Met Asp Leu Cys
                20                  25                  30
Ile Glu Cys Gln Ala Asn Gln Ala Ala Gly Leu Lys Asp Glu Cys Thr
            35                  40                  45
Val Ala Trp Gly Asn Cys Asn His Ala Phe His Phe His Cys Ile Ser
        50                  55                  60
Arg Trp Leu Lys Thr Arg Gln Val Cys Pro Leu Asp Asn Arg Glu Trp
65                  70                  75                  80
Glu Phe
```

```
<210> SEQ ID NO 33
<211> LENGTH: 82
<212> TYPE: PRT
<213> ORGANISM: Arabidopsis thaliana
<220> FEATURE:
<221> NAME/KEY: SIMILAR
<222> LOCATION: (1)..(82)
<223> OTHER INFORMATION: Partial protein sequence

<400> SEQUENCE: 33
```

Phe Glu Ile Lys Lys Trp Ser Ala Val Ala Leu Trp Ala Trp Asp Ile
1               5                   10                  15

Val Val Asp Asn Cys Ala Ile Cys Arg Asn His Ile Met Asp Leu Cys
                20                  25                  30

Ile Glu Cys Gln Ala Asn Gln Ala Ser Ala Thr Ser Glu Glu Cys Thr
            35                  40                  45

Val Ala Trp Gly Val Cys Asn His Ala Phe His Phe His Cys Ile Ser
        50                  55                  60

Arg Trp Leu Lys Thr Arg Gln Val Cys Pro Leu Asp Asn Ser Glu Trp
65                  70                  75                  80

Glu Phe

```
<210> SEQ ID NO 34
<211> LENGTH: 82
<212> TYPE: PRT
<213> ORGANISM: Schizosaccharomyces pombe
<220> FEATURE:
<221> NAME/KEY: SIMILAR
<222> LOCATION: (1)..(82)
<223> OTHER INFORMATION: Partial protein sequence

<400> SEQUENCE: 34
```

Phe Glu Ile Lys Lys Trp Asn Ala Val Ala Leu Trp Gln Trp Asp Ile
1               5                   10                  15

Val Val Asp Asn Cys Ala Ile Cys Arg Asn His Ile Met Asp Leu Cys
                20                  25                  30

Ile Glu Cys Gln Ala Asn Thr Asp Ser Ala Ala Ala Gln Glu Cys Thr
            35                  40                  45

Val Ala Trp Gly Thr Cys Asn His Ala Phe His Phe His Cys Ile Ser
        50                  55                  60

Arg Trp Leu Asn Thr Arg Asn Val Cys Pro Leu Asp Asn Arg Glu Trp
65                  70                  75                  80

Glu Phe

```
<210> SEQ ID NO 35
<211> LENGTH: 82
<212> TYPE: PRT
<213> ORGANISM: Saccharomyces cerevisiae
<220> FEATURE:
<221> NAME/KEY: SIMILAR
<222> LOCATION: (1)..(82)
<223> OTHER INFORMATION: Partial protein sequence

<400> SEQUENCE: 35
```

Phe Glu Ile Lys Lys Trp Thr Ala Val Ala Phe Trp Ser Trp Asp Ile
1               5                   10                  15

Ala Val Asp Asn Cys Ala Ile Cys Arg Asn His Ile Met Glu Pro Cys
                20                  25                  30

Ile Glu Cys Gln Pro Lys Ala Met Thr Asp Thr Asp Asn Glu Cys Val
            35                  40                  45

```
Ala Ala Trp Gly Val Cys Asn His Ala Phe His Leu His Cys Ile Asn
        50                  55                  60

Lys Trp Ile Lys Thr Arg Asp Ala Cys Pro Leu Asp Asn Gln Pro Trp
65                  70                  75                  80

Gln Leu

<210> SEQ ID NO 36
<211> LENGTH: 79
<212> TYPE: PRT
<213> ORGANISM: Homo sapiens
<220> FEATURE:
<221> NAME/KEY: SIMILAR
<222> LOCATION: (1)..(79)
<223> OTHER INFORMATION: Partial protein sequence

<400> SEQUENCE: 36

Phe Ser Leu Lys Lys Trp Asn Ala Val Ala Met Trp Ser Trp Asp Val
1               5                   10                  15

Glu Cys Asp Thr Cys Ala Ile Cys Arg Val Gln Val Met Asp Ala Cys
                20                  25                  30

Leu Arg Cys Gln Ala Glu Asn Lys Gln Glu Asp Cys Val Val Val Trp
            35                  40                  45

Gly Glu Cys Asn His Ser Phe His Asn Cys Cys Met Ser Leu Trp Val
        50                  55                  60

Lys Gln Asn Asn Arg Cys Pro Leu Cys Gln Gln Asp Trp Val Val
65                  70                  75

<210> SEQ ID NO 37
<211> LENGTH: 78
<212> TYPE: PRT
<213> ORGANISM: Caenorhabditis elegans
<220> FEATURE:
<221> NAME/KEY: SIMILAR
<222> LOCATION: (1)..(78)
<223> OTHER INFORMATION: Partial protein sequence

<400> SEQUENCE: 37

Phe Val Leu Lys Lys Trp Asn Ala Leu Ala Val Trp Ala Trp Asp Val
1               5                   10                  15

Glu Cys Asp Thr Cys Ala Ile Cys Arg Val His Leu Met Glu Glu Cys
                20                  25                  30

Leu Arg Cys Gln Ser Glu Pro Ser Ala Glu Cys Tyr Val Val Trp Gly
            35                  40                  45

Asp Cys Asn His Ser Phe His Cys Cys Met Thr Gln Trp Ile Arg
        50                  55                  60

Gln Asn Asn Arg Cys Pro Leu Cys Gln Lys Asp Trp Val Val
65                  70                  75

<210> SEQ ID NO 38
<211> LENGTH: 80
<212> TYPE: PRT
<213> ORGANISM: Homo sapiens
<220> FEATURE:
<221> NAME/KEY: SIMILAR
<222> LOCATION: (1)..(80)
<223> OTHER INFORMATION: Partial protein sequence

<400> SEQUENCE: 38

Val Lys Ile Lys Cys Trp Asn Gly Val Ala Thr Trp Leu Trp Val Ala
1               5                   10                  15

Asn Asp Glu Asn Cys Gly Ile Cys Arg Met Ala Phe Asn Gly Cys Cys
                20                  25                  30
```

```
Pro Asp Cys Lys Val Pro Gly Asp Asp Cys Pro Leu Val Trp Gly Gln
        35                  40                  45

Cys Ser His Cys Phe His Met His Cys Ile Leu Lys Trp Leu His Ala
    50                  55                  60

Gln Gln Val Gln Gln His Cys Pro Met Cys Arg Gln Glu Trp Lys Phe
65                  70                  75                  80

<210> SEQ ID NO 39
<211> LENGTH: 80
<212> TYPE: PRT
<213> ORGANISM: Drosophila melanogaster
<220> FEATURE:
<221> NAME/KEY: SIMILAR
<222> LOCATION: (1)..(80)
<223> OTHER INFORMATION: Partial protein sequence

<400> SEQUENCE: 39

Val Thr Ile Lys Ser Trp Thr Gly Val Ala Thr Trp Arg Trp Ile Ala
1               5                   10                  15

Asn Asp Glu Asn Cys Gly Ile Cys Arg Met Ser Phe Glu Ser Thr Cys
                20                  25                  30

Pro Glu Cys Ala Leu Pro Gly Asp Asp Cys Pro Leu Val Trp Gly Val
        35                  40                  45

Cys Ser His Cys Phe His Met His Cys Ile Val Lys Trp Leu Asn Leu
    50                  55                  60

Gln Pro Leu Asn Lys Gln Cys Pro Met Cys Arg Gln Ser Trp Lys Phe
65                  70                  75                  80

<210> SEQ ID NO 40
<211> LENGTH: 74
<212> TYPE: PRT
<213> ORGANISM: Caenorhabditis elegans
<220> FEATURE:
<221> NAME/KEY: SIMILAR
<222> LOCATION: (1)..(74)
<223> OTHER INFORMATION: Partial protein sequence

<400> SEQUENCE: 40

Ile Thr Val Lys Lys Leu His Val Cys Gly Glu Trp Lys Trp Leu Asp
1               5                   10                  15

Thr Cys Gly Ile Cys Arg Met Glu Phe Glu Ser Ala Cys Asn Met Cys
                20                  25                  30

Lys Phe Pro Gly Asp Asp Cys Pro Leu Val Leu Gly Ile Cys Arg His
        35                  40                  45

Ala Phe His Arg His Cys Ile Asp Lys Trp Ile Gln Pro Arg Ala Gln
    50                  55                  60

Cys Pro Leu Cys Arg Gln Asp Trp Thr Ile
65                  70

<210> SEQ ID NO 41
<211> LENGTH: 76
<212> TYPE: PRT
<213> ORGANISM: Saccharomyces cerevisiae
<220> FEATURE:
<221> NAME/KEY: SIMILAR
<222> LOCATION: (1)..(76)
<223> OTHER INFORMATION: Partial protein sequence

<400> SEQUENCE: 41

Val Lys Ile Asn Glu Val His Ser Val Phe Ala Trp Ser Trp Asp Val
1               5                   10                  15
```

-continued

```
Cys Gly Ile Cys Arg Ala Ser Tyr Asn Gly Thr Cys Pro Ser Cys Lys
            20                  25                  30

Phe Pro Gly Asp Gln Cys Pro Leu Val Ile Gly Leu Cys His His Asn
            35                  40                  45

Phe His Asp His Cys Ile Tyr Arg Trp Leu Asp Thr Pro Thr Ser Lys
        50                  55                  60

Gly Leu Cys Pro Met Cys Arg Gln Thr Phe Gln Leu
65                  70                  75
```

ISOLATED DNA ENCODING CULLIN REGULATORS ROC1 AND ROC2, ISOLATED PROTEINS ENCODED BY THE SAME, AND METHODS UTILIZING THE SAME

RELATED APPLICATIONS

This application is a divisional of and claims priority to U.S. application Ser. No. 09/541,462, filed Mar. 31, 2000, allowed, now U.S. Pat. No. 7,078,203, which claims the benefit of U.S. Provisional Application No. 60/127,261, filed Mar. 31, 1999, and U.S. Provisional Application No. 60/166,927, filed Nov. 22, 1999, the entire contents of each of which are incorporated by reference herein.

STATEMENT OF FEDERAL SUPPORT

This invention was made with government support under grant number RO1 CA65572-01 from the National Institutes of Health. The United States government has certain rights to this invention.

FIELD OF THE INVENTION

This invention relates to nucleic acid and amino acid sequences of cullin regulators that are associated with ubiquitin ligase activity, and to methods utilizing these sequences.

BACKGROUND OF THE INVENTION

The ubiquitin-dependent proteolytic process regulates many short lived intracellular proteins, whose concentrations change promptly as the result of alterations in cellular physiological conditions. See Hochstrasser, M. et al. (1996) *Annu. Rev. Genet.* 30, 405-439.; King, R. W., et al. (1996) *Science* 274, 1652-1659; Hershko, A. et al. (1997) *Curr. Opin. Cell Blot.* 9, 788-799. In addition to performing "housekeeping" functions such as homeostasis and the removal of misfolded proteins, this proteolytic process is involved in the degradation of many regulatory proteins, such as cyclins, CDK inhibitors, transcription factors, and signal transducers. In brief, ubiquitin-mediated proteolysis begins with activation of ubiquitin, a 76-amino acid protein expressed in all eukaryotic cells, in an ATP-dependent manner by an ubiquitin-activating enzyme (E1 or Uba). The activated ubiquitin forms a high energy thiolester bond with E1 and is passed to a cysteine residue also via a thiolester bond within an ubiquitin-conjugating enzyme designated as an E2 or Ubc. E2-linked ubiquitin is then transferred to a side chain amino group of a lysine residue in the substrate to form a terminal isopeptide bond, either directly or often indirectly targeted by a ubiquitin ligase known as E3. Substrate proteins can be linked to a single ubiquitin (monoubiquitinated) or multiple ubiquitin molecules (polyu biquitinated). The significance of monoubiquitinated conjugates is not clear since they do not appear to be short-lived. Successive covalent ligations of additional ubiquitins to the Lys 48 of the preceding ubiquitin via an isopeptide bond results in polyubiquitinated conjugates which are rapidly detected and degraded by the 26S proteosome. E3 is functionally, rather than structurally, defined as an ubiquitin ligase activity that is both necessary and sufficient for transfer of ubiquitin from a ubiquitin-charged E2 to a substrate, and is further believed to be involved in many polyubiquitination reactions by providing substrate specificity. Because most polyubiquitinated proteins are indiscriminately delivered to the 26S proteosome for degradation, elucidating the mechanism and regulation of E3 ligase activities has become a critical issue central to the understanding of regulated proteolysis.

The cullin family of protiens potentially form a large number of distint E3s as indicated by the existence of a multi-gene family and by the assembly of yeast CDC53 into at least three distinct E3 complexes: with SKP1-CDC4, with SKP1-GRR1 and likely with SKP1-MET30 to mediate the ubiquitination of SIC1, CLN and SWE1 proteins, respectively. See, e.g., Skowyra, D., et al.,(1997) *Cell* 91, 209-219; Feldman, R. M. R. (1997) *Cell* 91,221-230; and Kaiser, P. et.al., (1998) *Genes & Dev.* 12, 2587-2597. Through targeting different substrates, different cullins function in a variety of diverse cellular processes. For example, CDC53 is required for S phase entry (Mathias, N. et al., (1996) *Mol. Cell Biol.* 16, 6634-6643; for coupling glucose sensing to gene expression and the cell cycle (Li, F. N. and Johnston, M. (1997) *EMBO J.* 16, 5629-5638; and possibly for activating mitotic CLB-CDC28 activity (Kaiser, P.et al., (1998) *Genes & Dev.* 12, 2587-2597). As set forth in more detail below, the *C. elegans* cul-1 mutant displays a hyperplasia phenotype. Human CUL2 is associated with the tumor suppressor VHL (von Hippel-Lindau) implicated in the regulation of the stability of hypoxia-induced mRNA (see Pause, A., et al., (1997) *Proc. Natl. Acad. Sci. USA*. 94, 2146-2161; Lonergan, K. M. et al., (1998) *Mol. Cell Biol*. 18, 732-741. Human CUL4A is implicated in oncogenesis by its genomic amplification and overexpression in breast cancers (Chen, L-C., et al., (1998) *Cancer Res*. 58, 3677-3683), and deficiency of the cullin-related APC2 results in mitotic arrest (Zachariae, W. et al., (1998) *Science* 279, 1216-1219; Yu, H., et al., *Current Biology* 6, 455-466).

The knowledge of E3 ubiquitin ligases is presently limited. Among the few characterized E3 ligases are the N-end rule ubiquitin ligase E3α/Ubr1 that recognize proteins by binding to the basic or hydrophobic residues at the amino-termini of substrate proteins (reviewed in Varshavsky, A. (1996) *Proc. Natl Acad. Sci U.S.A.* 93, 12142-12149); the HECT (homologous to E6-AP carboxy terminus) domain proteins represented by the mammalian E6AP-E6 complex which functions as a ubiquitin-ligase for p53 (see Scheffner, M. et al., (1993) *Cell* 75, 495-505; Huibregtse, J. M., et al. (1995) *Proc. Natl. Acad. Sci. USA* 92, 2563-2567; Scheffner, M.et al. (1995) *Nature* 373, 81-83); and the APC (anaphase-promoting complex or cyclosome), a 20S complex that consists of 8 to 12 subunits and is required for both entry into anaphase as well as exit from mitosis (see King, R. W., Deshaies, *Science* 274, 1652-1659).

The APC plays a crucial role in regulating the passage of cells through anaphase by promoting ubiquitin-dependent proteolysis of many proteins. The APC destroys the mitotic B-type cyclin for inactivation of CDC2 kinase activity and initiating cytokinesis. The APC is also required for degradation of other proteins for sister chromatid separation and spindle disassembly, including the anaphase inhibitors PDS1 (Cohen-Fix, O., et al.(1996) *Genes & Dev.* 10, 3081-3093) and CUT2 (Funabiki, H., et al. (1996) *Nature* 381, 438-441), ASE1 (Juang, Y-L. et al. (1997) *Science* 275, 1311-1314) and the cohesion protein SCC1P (Michaelis, C. et al., (1997) *Cell* 91, 35-45). All known proteins degraded by the APC contain a conserved nine amino acid stretch commonly known as the destruction box that is necessary for their ubiquitination and subsequent degradation (Glotzer, M., et al. (1991) *Nature* 349, 132-138). Proteins that are degraded during G1, ranging from G1 cyclins and CDK inhibitors to transcription factors, do not contain the conserved destruction box or any other common structural motif. Instead, substrate phosphorylation appears to play an important role in targeting their interaction with E3 for subsequent ubiquitination. Genetic and biochemical analysis has identified in yeast an E3-like activity, dubbed as the SCF, that plays a key role in regulating G1 progression. The SCF consists of at least three subunits, SKP1, CDC53/cullin and an F-box containing protein, in which SKP1 functions as an adaptor to connect CDC53 to the F-box protein which binds directly to the substrate (Feldman, R. M. R., et al., (1997) *Cell* 91, 221-230; Bai, C., et al. (1996) *Cell* 86,263-274; Willems, A. R., (1996) *Cell* 86, 453-463; Verma, R.(1997) *Science* 278, 455-460; Skowyra, D., (1997) *Cell* 91, 209-219).

In a screen for mutants with excess postembryonic cell divisions in *C. elegans*, the gene cullin-1 (CUL1), was identified. Loss of function of this gene caused hyperplasia of all tissues as a result of the failure to properly exit from the cell cycle. See Kipreos, E. T., et al., (1996) *Cell* 85, 829-839. CUL1 represents an evolutionarily conserved multigene family that includes at least seven members in *C. elegans*, six in humans, and three in budding yeast including Cdc53p (Kipreos, et al., supra, and Mathias, N. et al., (1996) *Mol. Cell Biol.* 16, 6634-6643). Like yeast CDC53, human cullin 1 directly binds to SKP1 to form a multi-subunit complex with SKP2 (an F box protein), cyclin A and CDK2 (Lisztwan, J. et al., (1998) *EMBO J.* 17,368-383; Michel, J. and Xiong, Y. (1998) *Cell Growth. Differ.* 9, 439-445; Lyapina, S. A., et al. (1998) *Proc. Natl. Acad. Sci. USA* 95, 7451-7456; and Yu, Z. K. et al. (1998) *Proc. Natl. Acad. Sci U.S.A.* 95, 11324-11329), and can assemble into functional, chimeric ubiquitin ligase complexes with yeast SCF components. Recently, a subunit of the mitotic APC E3 complex, APC2, was found to contain limited sequence similarity to CDC53/cullins (Zachariae, W. et al., (1998) *Science* 279, 1216-1219; Yu, H. et al., (1998) *Science* 279, 1219-1222.). These findings, together with the fact that no obvious structural similarity between other components of the SCF and APC complexes exists, underscore an important and conserved role for cullin proteins in ubiquitin-mediated proteolysis, possibly as an intrinsic partner of ubiquitin ligases. However, despite extensive investigations of the APC and SCF E3 ligases, the nature of ubiquitin ligases has thus far been elusive. It still remains to be determined whether there is a "ligase" in the APC and SCF. Whether the cullin proteins act as ubiquitin ligases to catalyze isopeptide bond formation or as scaffold proteins to bring together E2-Ub and substrates together is heretofore not described.

Equally important as the mechanism that determines the substrate specificity is the regulation of E3 ligases, which is presently poorly understood. The activity of the APC is cell-cycle regulated, and active from anaphase until late G1. See Amon, A. (1994) *Cell* 77, 1037-1050; King, R., et al., (1995) supra; Brandeis, M. and Hunt, T. (1996) *EMBO J.* 15, 5280-5289. The principle regulation is probably provided by subunit rearrangements such as CDC20 and CDH1 binding (Visintin, et al., (1997) *Science* 278, 460-463; Schwab, M. (1997) *Cell* 90, 683-693; Sigrist, S. J. and Lehner, C. F. (1997) *Cell* 90, 671-681; and Fang, G. (1998) *Mol. Cell* 2, 163-171). Phosphorylation of certain subunits may also play an important, but supplementary role (Lahav-Baratz, S., *Proc. Natl. Acad. Sci. USA* 92, 9303-9307; Peters, J.-M. et al. (1996) *Science* 274, 1199-1201). Regulation of CDC53 and cullin-mediated E3 ligase activity during interphase is heretofore not described.

SUMMARY OF THE INVENTION

The present inventors have identified a family of two closely related RING finger proteins, ROC1 and ROC2, that are similar to APC11, a subunit of the APC complex. ROC1 and ROC2 commonly interact with all cullin proteins, while APC11 specifically interacts with APC2. ROC1 functions in vivo as an essential regulator of CDK inhibitor Sic1 degradation by the SCF pathway. Additionally, the inventors have found that ROC-cullin constitutes the catalytic ubiquitin ligase. Although the inventors do not wish to be bound to any theory of the invention, it is thought that dimeric complexes of ROC1-cullins and APC11-APC2 function as ubiquitin ligases during interphase and mitosis, respectively.

Accordingly, the invention provides an isolated polynucleotide sequence encoding the protein ROC1. The polynucleotide sequence may be selected from the group consisting of:
   (a) DNA having the nucleotide sequence given herein as SEQ ID NO:1 (which encodes the protein having the amino acid sequence given herein as SEQ ID NO:2);
   (b) polynucleotides that hybridize to DNA of (a) above (e.g., under stringent conditions) and which encode the protein ROC1; and
   (c) polynucleotides that differ from the DNA of (a) or (b) above due to the degeneracy of the genetic code, and which encode the protein ROC1 encoded by a DNA of (a) or (b) above.

The present invention further provides an expression vector containing at least a fragment of any of the claimed polynucleotide sequences. In yet another aspect, the expression vector containing the polynucleotide sequence is contained within a host cell.

The invention further provides a protein or fragment thereof encoded by a polynucleotide as given above (e.g., the protein provided herein as SEQ ID NO: 2). Such proteins may be isolated and/or purified in accordance with known techniques.

The invention also provides a method for producing a polypeptide comprising the amino acid sequence of SEQ ID NO:2, or a fragment thereof, the method comprising the steps of: a) culturing the host cell containing an expression vector containing at least a fragment of the polynucleotide sequence encoding ROC1 under conditions suitable for the expression of the polypeptide; and b) recovering the polypeptide from the host cell culture.

The invention also provides an antibody (e.g., a polyclonal antibody, a monoclonal antibody) which specifically binds to a protein as given above.

The invention provides an antisense oligonucleotide complementary to a polynucleotide sequence as given above and having a length sufficient to hybridize thereto under physiological conditions. DNA encoding such an antisense oligonucleotide, and a nucleic acid construct having a promoter and a heterologous nucleic acid operably linked to said promoter (wherein the heterologous nucleic acid is a DNA encoding such an antisense oligonucleotide) is also an aspect of the invention.

The invention also provides a method for detecting a polynucleotide which encodes ROC1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding ROC1 in the biological sample. In one aspect, the nucleic acid material of the biological sample is amplified by the polymerase chain reaction prior to hybridization.

Further, the invention provides an isolated polynucleotide sequence encoding the protein ROC2. The polynucleotide sequence may be selected from the group consisting of:

(a) DNA having the nucleotide sequence given herein as SEQ ID NO:3 (which encodes the protein having the amino acid sequence given herein as SEQ ID NO:4);

(d) polynucleotides that hybridize to DNA of (a) above (e.g., under stringent conditions) and which encode the protein ROC1 and (e) polynucleotides that differ from the DNA of (a) or (b) above due to the degeneracy of the genetic code, and which encodes the protein ROC 1 encoded by a DNA of (a) or (b) above.

The present invention further provides an expression vector containing at least a fragment of any of the claimed polynucleotide sequences. In yet another aspect, the expression vector containing the polynucleotide sequence is contained within a host cell.

The invention further provides a protein or fragment thereof encoded by a polynucleotide as given above (e.g., the protein provided herein as SEQ ID NO: 4). Such proteins may be isolated and/or purified in accordance with known techniques.

The invention also provides a method for producing a polypeptide comprising the amino acid sequence of SEQ ID NO:4, or a fragment thereof, the method comprising the steps of: a) culturing the host cell containing an expression vector containing at least a fragment of the polynucleotide sequence encoding ROC2 under conditions suitable for the expression of the polypeptide; and b) recovering the polypeptide from the host cell culture.

The invention also provides an antibody (e.g., a polyclonal antibody, a monoclonal antibody) which specifically binds to a protein as given above.

The invention provides an antisense oligonucleotide complementary to a polynucleotide as given above and having a length sufficient to hybridize thereto under physiological conditions. DNA encoding such an antisense oligonucleotide, and a nucleic acid construct having a promoter and a heterologous nucleic acid operably linked to said promoter (wherein the heterologous nucleic acid is a DNA encoding such an antisense oligonucleotide) is also an aspect of the invention.

The invention also provides a method for detecting a polynucleotide which encodes ROC2 in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding ROC2 in the biological sample. In one aspect, the nucleic acid material of the biological sample is amplified by the polymerase chain reaction prior to hybridization.

The invention provides methods for screening bioactive agents (the term "agent" and grammatical equivalents thereof being used interchangeably with the term "compound" and the grammatical equivalents thereof) that are capable of binding to a ROC protein, wherein a ROC protein and a candidate bioactive agent are combined. The binding of the candidate bioactive agent is then determined. Methods of screening bioactive agents capable of interfering with the binding of ROC proteins, or of modulating the activity of a ROC protein, are also aspects of the present invention. Such screening methods are capable of identifying compounds that have pharmacological (pharmaceutical) activity. Pharmaceutical formulations comprising such pharmacologically active compounds and methods of administering the same are another aspect of this invention. Yet another aspect of the present invention is the use of a pharmacologically active compound identified by the methods described herein for the manufacture of a medicament for the prophylactic or therapeutic use in a subject or host.

The foregoing and other objects and aspects of the present invention are explained in detail in the specification set forth below.

BRIEF DESCRIPTION OF THE DRAWINGS

FIGS. 1A and 1B illustrate that ROC1 interacts with members of the cullin family. In the experiments illustrated in FIG. 1A, yeast HF7c cells were co-transformed with plasmids expressing indicated proteins (key) and plated onto media lacking leucine and tryptophan (−LW) to verify the presence of both bait (Leu+) and prey (Trp+) plasmids; or onto media lacking leucine, tryptophan and histidine (−LWH) to assay for interactions between bait and prey proteins.

FIG. 1B illustrates that ROC1 interacts with the C-terminal portion of CUL1. HF7c yeast cells were co-transformed with plasmids expressing indicated proteins. Protein-protein interaction was assayed as described in herein.

FIG. 2A sets forth the nucleotide sequence (SEQ ID NO:1) and the amino acid sequence (SEQ ID NO:2) of human ROC1. The stop codon is indicated by an asterisk.

FIG. 2B illustrates the sequence comparison of ROC/APC11 family of proteins from representative organisms: human (Hs, *Homo sapiens*), fruit fly (Dmn: *Drosophila melanogaster*), nematodes (Ce: *Caenorhabditis elegans*), mouse ear cress (At: *Arabidopsis thaliana*), fission yeast (Sp: *Schizosaccharomyces pombe*), and budding yeast (Sc: *Saccharomyces cerevisiae*). Residues that are identical among all sequences are presented in bold type. The number in the bracket of certain sequences indicates the length omitted. The number preceding and following each sequence indicates the position of the first amino acid residue in each gene and the total length of each protein, respectively.

Figure 3A:
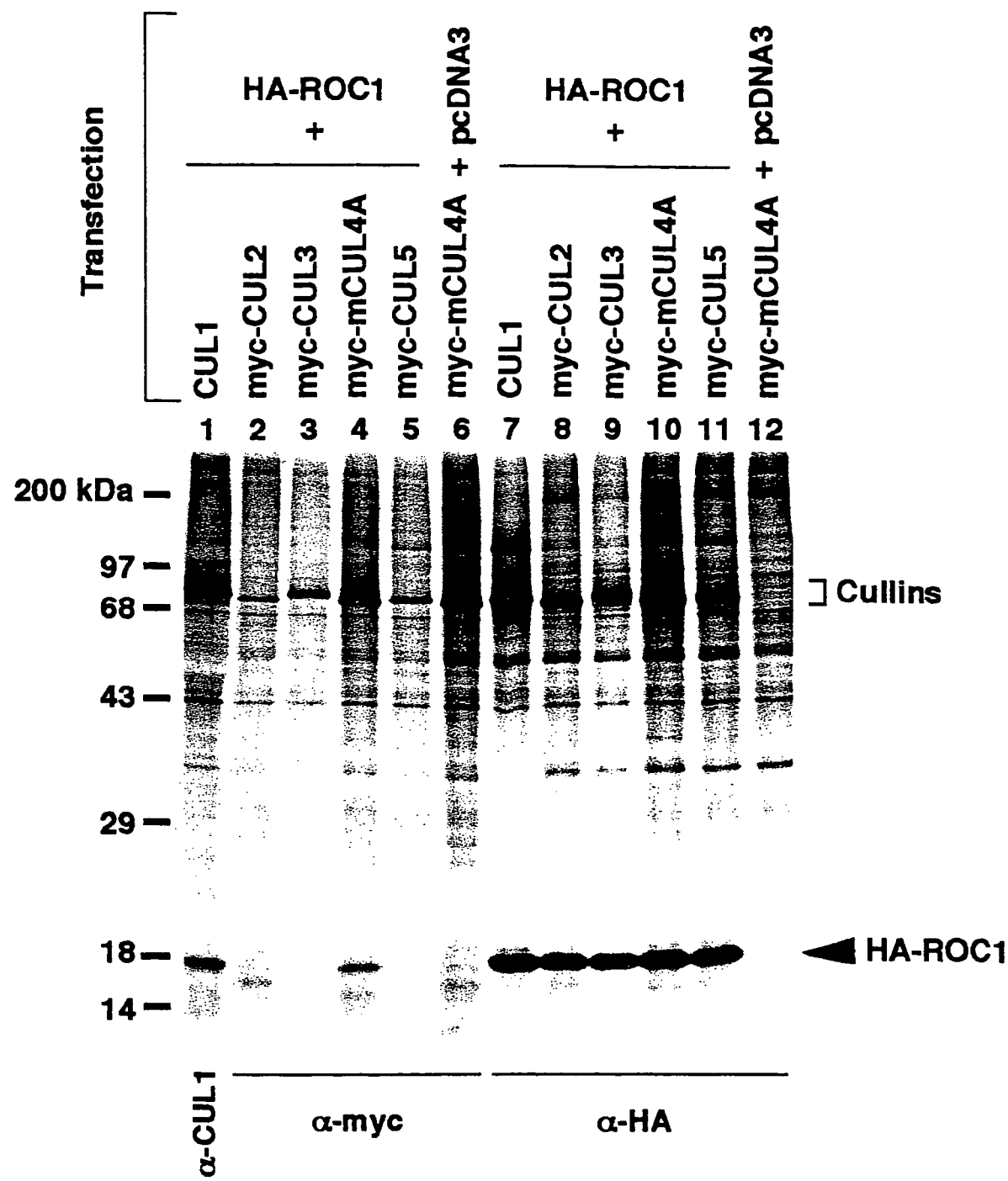
FIGS. 3A, 3B and 3C illustrate the in vivo association of ROC1 with cullins. In the experiments shown in FIG. 3A, [$^{35}$S]-methionine labeled lysates were prepared from HeLa cells transfected with plasmids expressing the indicated proteins. Lysates were divided into two equal amounts and immunoprecipitated with indicated antibodies and resolved by SDS-PAGE. For the experiments illustrated in FIG. 3B [$^{35}$S]-methionine labeled, in vitro translated ROC1 (lane 1), mixture of ROC1 and CUL1 (lane 2), or cell lysates from HeLa and Saos-2 cells were immunoprecipitated with anti-ROC1 antibody with (+) or without (−) pre-incubation of the competing ROC1 antigen peptide as indicated at the top of each lane. After several washings, precipitates were resolved by SDS-PAGE.
Figure 3B:
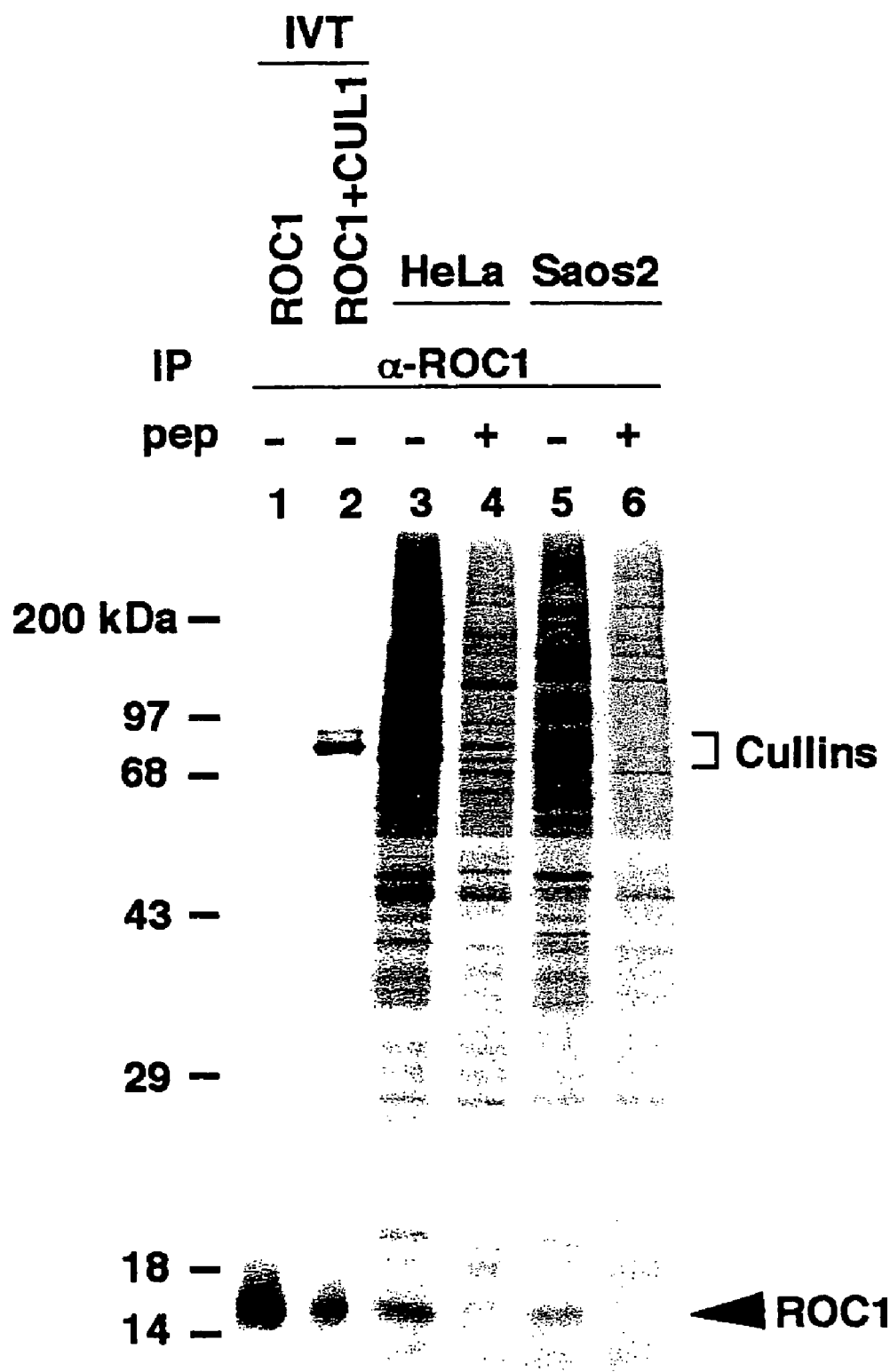
Figure 3C:
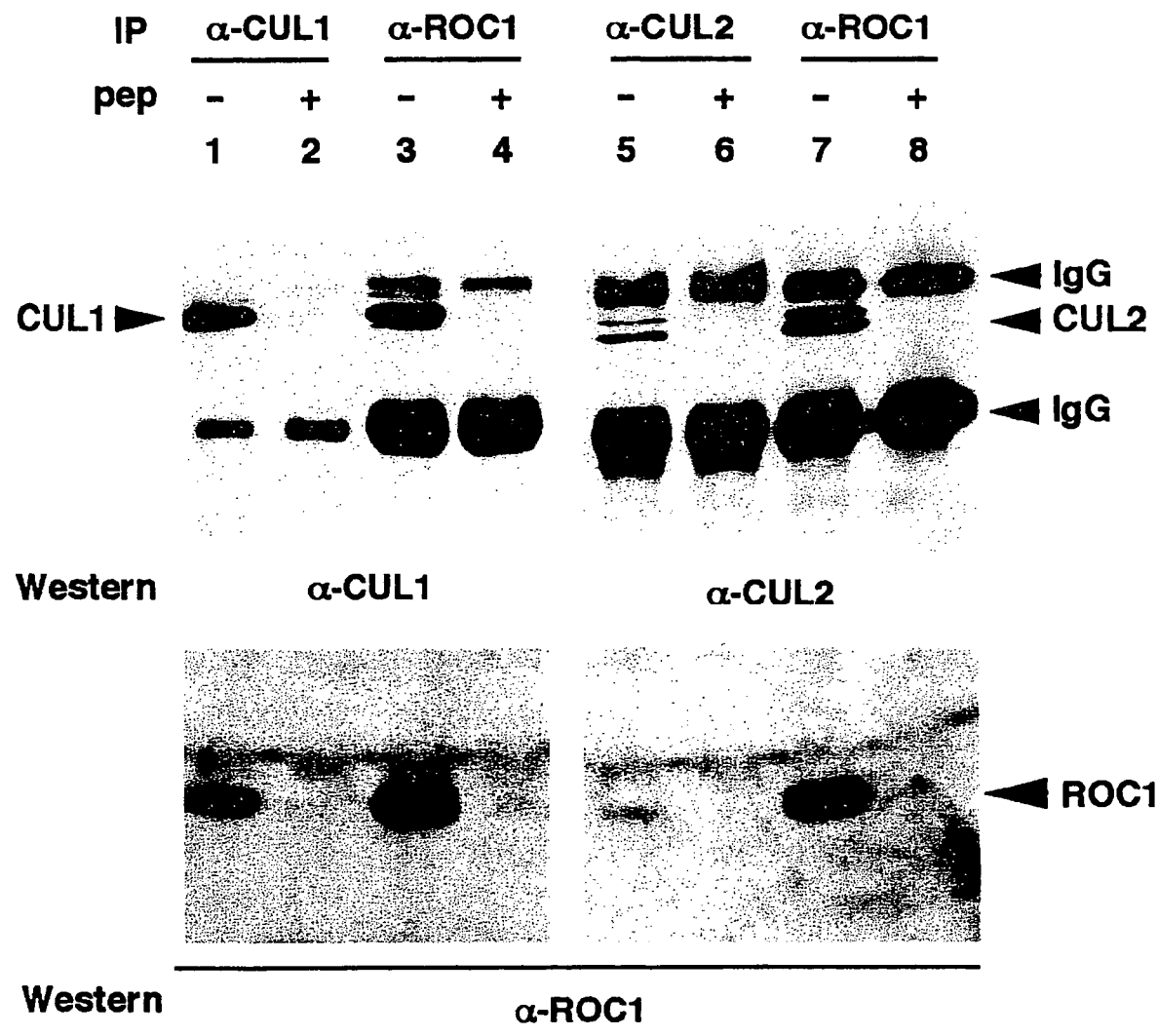

For the experiments illustrated in FIG. 3C, total cell lysates prepared from HeLa cells were immunoprecipitated with indicated antibodies with (+) or without (−) competing antigen peptide. After SDS-PAGE, proteins were transferred to nitrocellulose, and analyzed by Western analysis using antibodies to CUL1 (lanes 1 to 4, top panel), to CUL2 (lanes 5 to 8, top panel) or to ROC1 (bottom panel).

Figure 4C:
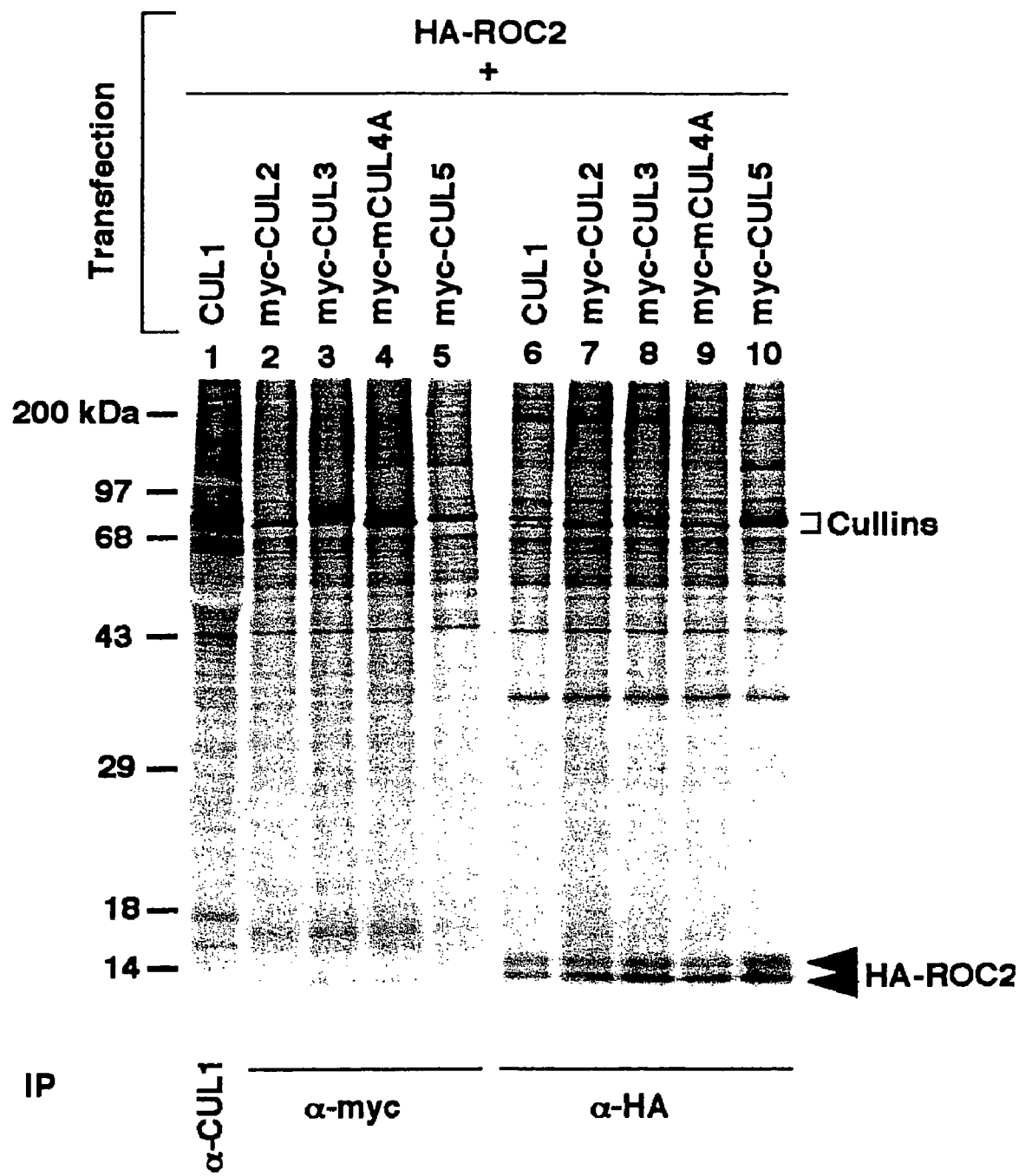
Figure 4D:
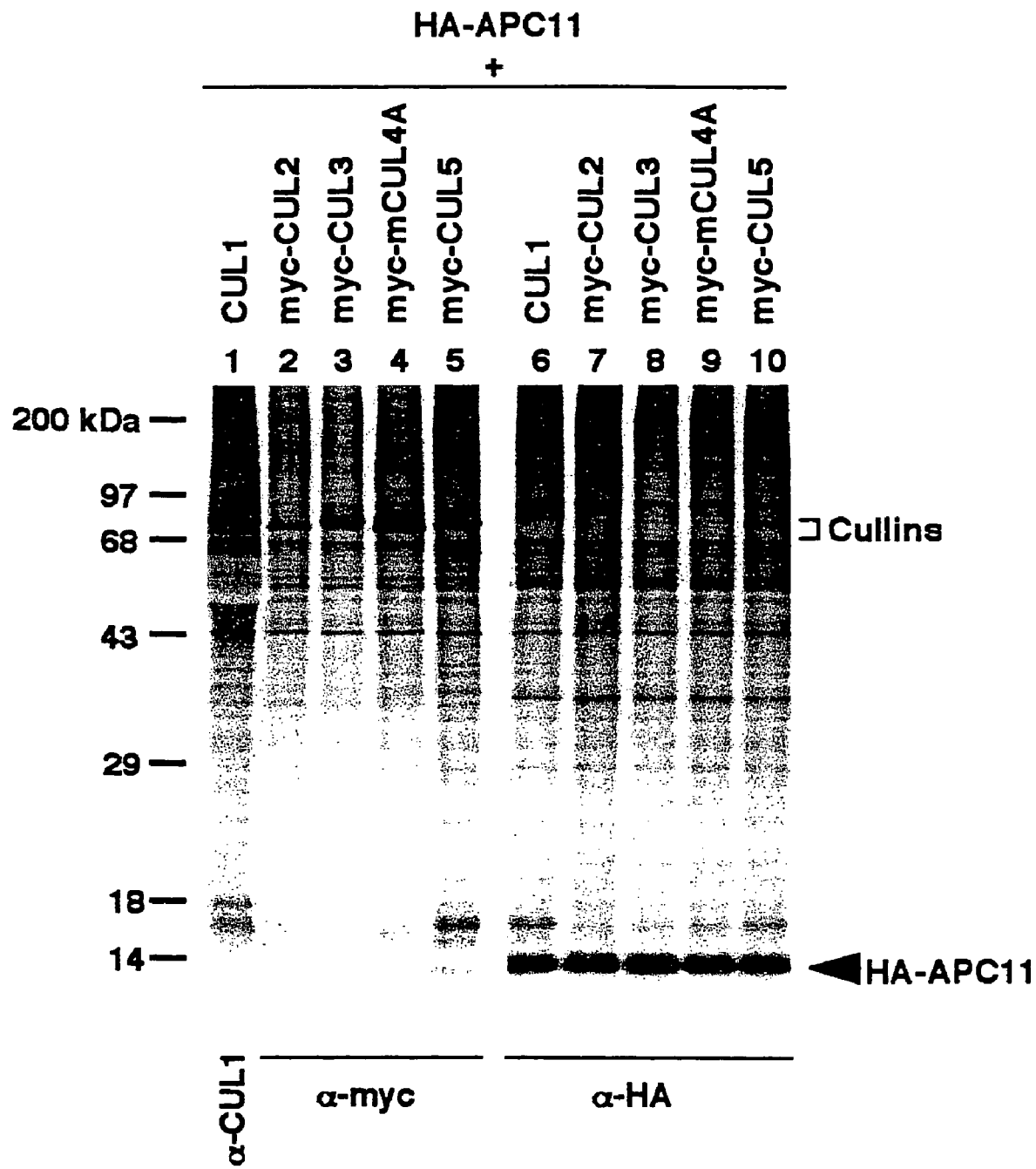

FIG. 4A-4E illustrate that ROC2 and APC11 selectively interact with cullins and APC2. In the experiments shown in FIGS. 4A and 4B HF7c yeast cells were co-transformed with plasmids expressing human ROC2 or human APC11 and various cullins. pGBT8-PCNA and pGAD vector plasmid were included as negative controls. Protein-protein interactions were determined by the yeast two-hybrid assay as described herein. FIG. 4C and FIG. 4D illustrate the interaction between ROC2, APC11 and cullin family proteins in mammalian cells. HA-tagged ROC2 or APC11 were co-transfected with vectors expressing CUL1 or myc-tagged individual cullin proteins into HeLa cells. Two days after transfection, cells were pulse labeled for 2 hours with [$^{35}$S]-methionine. Cell lysates prepared from the labeled cells were divided into two equal amounts, immunoprecipitated with the indicated antibodies and resolved by SDS-PAGE. All five cullin proteins were co-precipitated with HA-ROC2, but only CUL-5 co-precipitated with APC11.

Figure 4E:
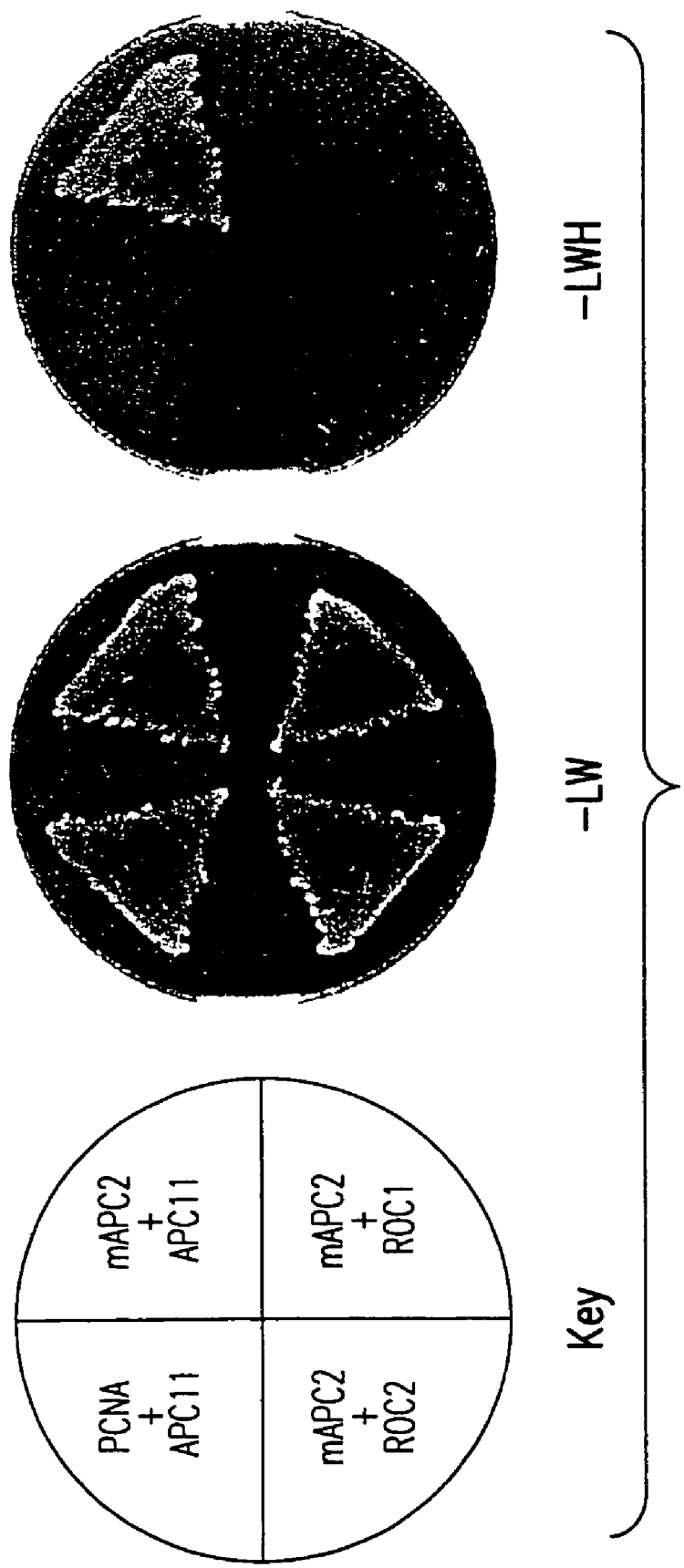

In the experiments shown in FIG. 4E Selective interaction between APC2 and ROC or APC11. HF7c yeast cells were co-transformed with plasmids expressing indicated proteins (key). Protein-protein interaction was determined by the yeast two-hybrid assay using selective medium lacking histidine (−LWH) supplemented with 5 mM 3-AT to suppress the low trans-activating activity of GAL4BD-APC2 fusion protein ("self-activation").

Figure 5B:
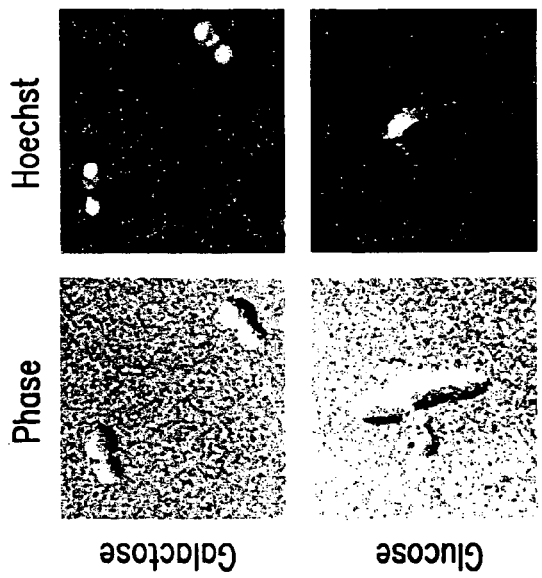
Figure 5A:
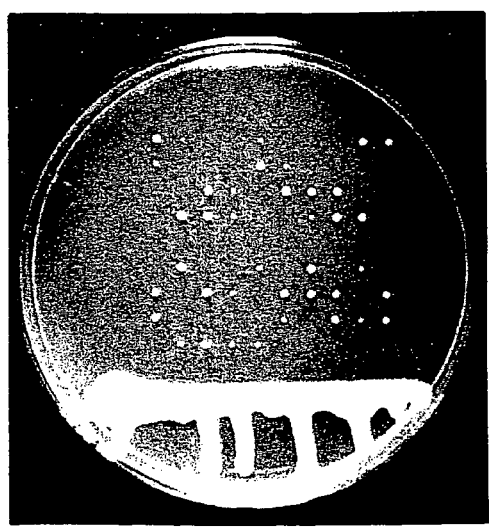

FIGS. 5A-5F illustrates the function of ROC1 in yeast. FIG. 5A illustrates that ScROC1 is an essential gene. Twenty tetrads from a +/roc1:kanR sporulated culture were dissected onto YPD plates, as shown.

FIG. 5B illustrates depletion of ScROC1p results in multi-budded cells. GAL-HA3-ScROC1 haploids were cultured in 2% galactose plus 2% raffinose (top panels) or 2% glucose (bottom panels) for 24 hours. DNA was stained using Hoechst dye.

Figure 5C:
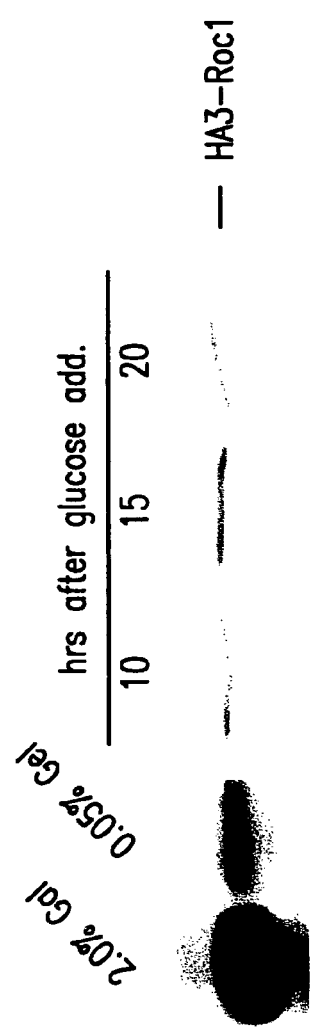

FIG. 5C illustrates depletion of ScROC1p. GAL-HA3-ScROC1 yeast cells were grown in either 2%, 0.05% galactose plus 2% raffinose or 2% glucose for different length of time as indicated. Cell lysates were resolved on an SDS-PAGE gel, transferred to nitrocellulose and blotted with anti-HA antibody to detect HA3-ROC1.

Figure 5D:
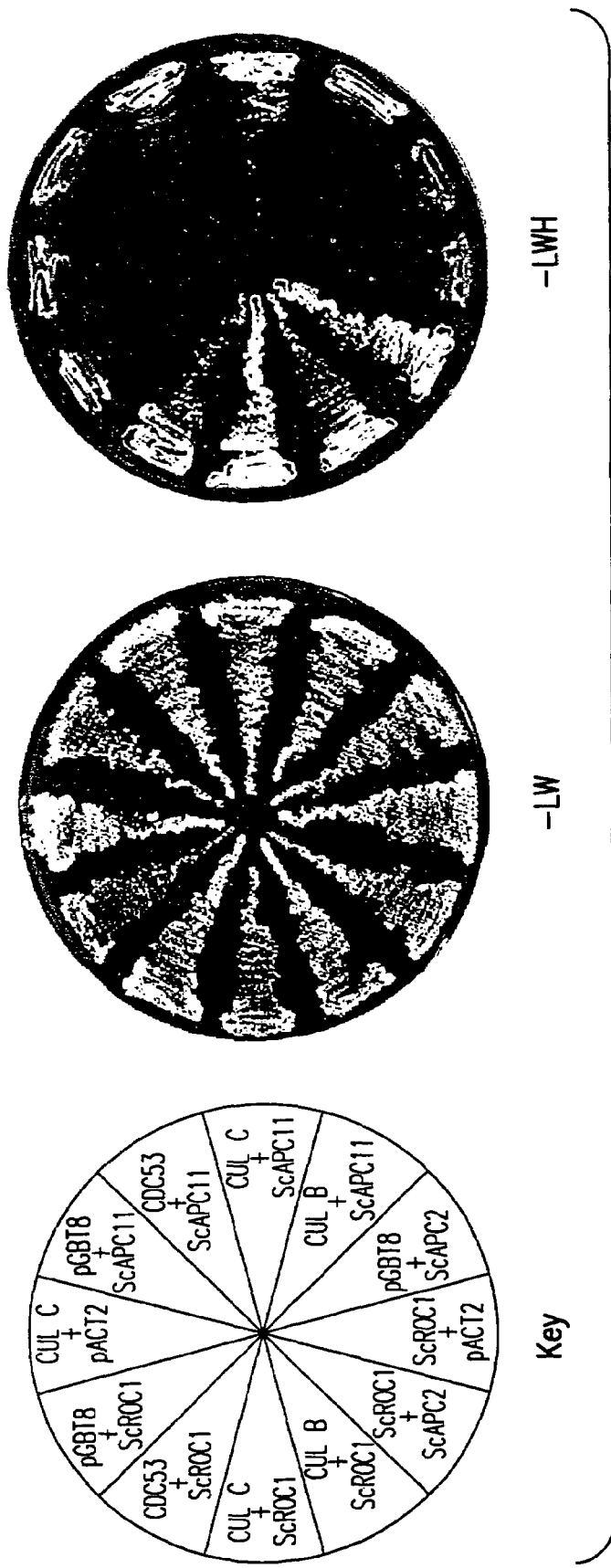

FIG. 5D illustrates that ScROC1 interacts with all yeast cullins. HF7c cells (his3-200, leu2-3, trp1-901, GAL4A-lacZ, GAL1-HIS3) were co-transformed with plasmids expressing indicated proteins (key). Protein-protein interactions were determined by the yeast two-hybrid assay as described in FIG. 1A.

Figure 5E:

FIG. 5E shows that human ROC1 and human ROC2 can rescue the multibudded phenotype resulting from ScROC1p deletion. GAL-HA3-ScROC1 haploids were transformed with pADH-414 vector, pADH-414-ScROC1, pADH-ScAPC11, pADH-hROC1 or pADH-hROC2. Transformants were streaked onto selective plates containing 2% glucose and grown for 24 hours when the yeast cells demonstrate a multiple elongated phenotype. Cells were formaldehyde fixed before photography.

Figure 5F:
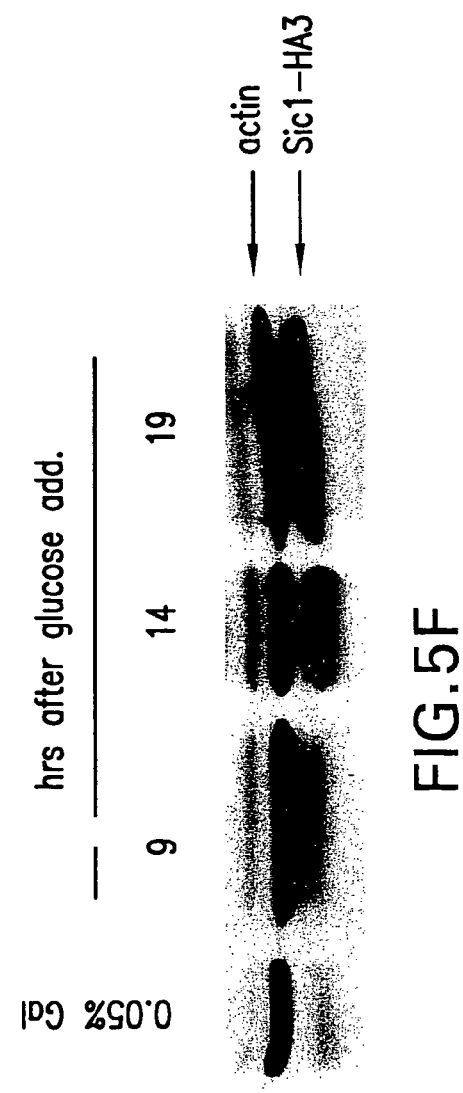

FIG. 5F illustrates that Sic 1 p accumulates in yeast depleted of ScROC1p. GAL-HA3-ScROC1/SIC1-HA3 yeast cells were grown in either 0.05% galactose or 2% glucose for different length of time as indicated. Cell lysates were resolved on an SDS-PAGE gel, transferred to nitrocellulose and blotted with anti-HA antibody to detect Sic1-HA3 and with anti-actin antibody to detect action to verify equal protein loading.

Figure 6A:
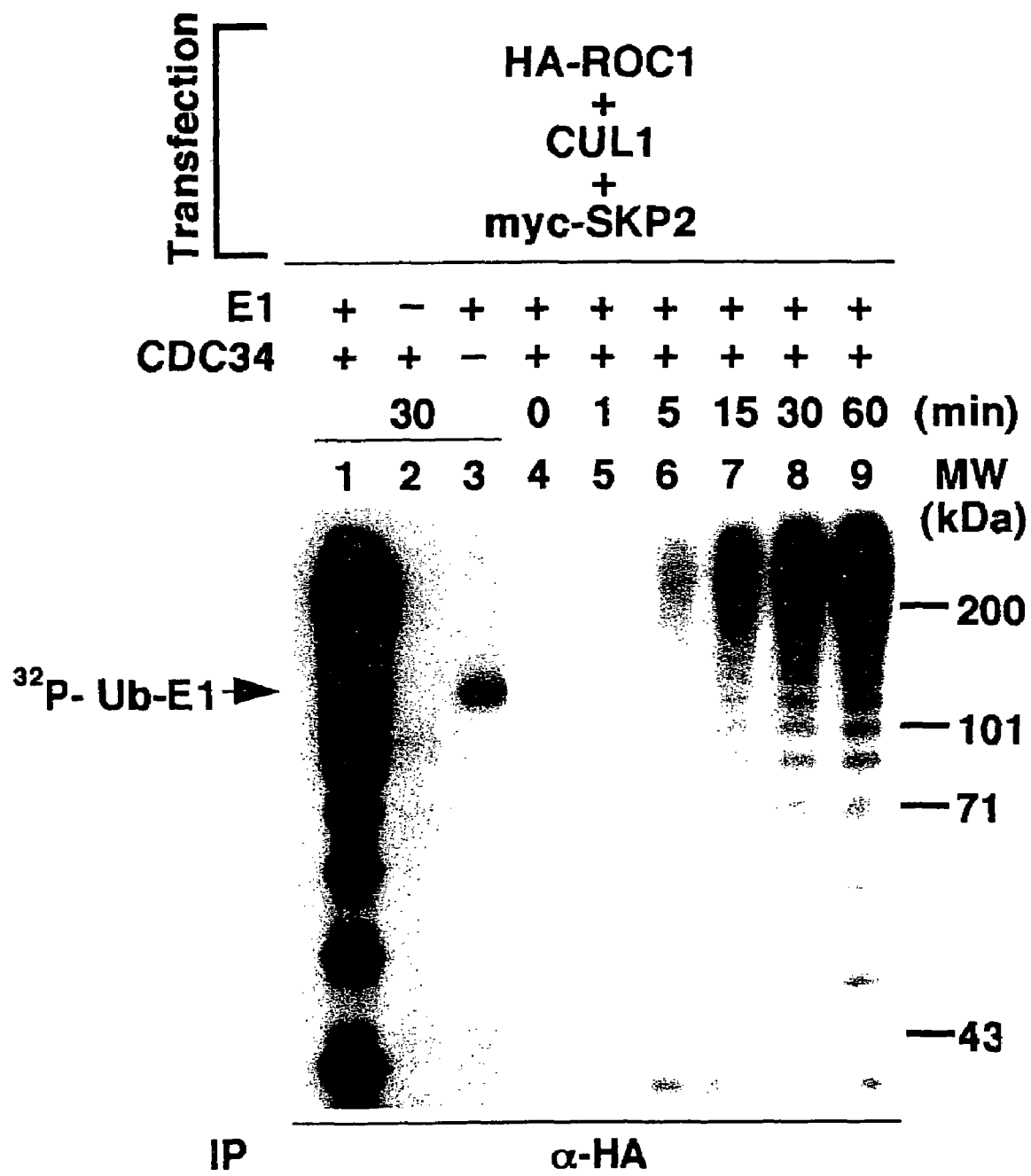

FIGS. 6A-6C illustrates that ROC1 stimulates cullin-dependent ubiquitin ligase activity. FIG. 6A illustrates that lysates (1 mg of total proteins) from human 293T cells transiently transfected with plasmids expressing indicated proteins were mixed with protein A beads linked to anti-HA antibodies. HA-immunocomplexes immobilized on the beads were washed and then mixed with purified E1, E2 CD34 (unless otherwise indicated), $^{32}$P-labeled ubiquitin (ub) and ATP. After 30 minutes incubation (unless otherwise specified) at 37° C., the reactions were terminated by boiling the samples in the presence of SDS and DTT and mixtures were resolved by SDS-PAGE, followed by autoradiography. FIG. 6B illustrates that ubiquitin ligase activity was assayed as in (A) using lysates derived from cells transfected with plasmids expressing different combination of proteins as indicated. FIG. 6C illustrates in vivo ubiquitin ligase activity. Lysates from un-transfected human HeLa or 293T cells were immunoprecipated with antibodies to either ROC1, APC11 or CUL1 as indicated with (lane 4) or without competing peptide. Ubiquitin ligase activity was assayed as described herein.

DETAILED DESCRIPTION OF THE INVENTION

The present invention will now be described more fully hereinafter with reference to the accompanying figures, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 C.F.R §1.822 and established usage. See, e.g., Patent In User Manual, 99-102 (November 1990) (U.S. Patent and Trademark Office).

ROC1 and ROC2 (referred to herein as the "ROC proteins"), as used herein, refer to the amino acid sequences of substantially purified ROC1 and ROC2 obtained from any species, particularly mammalian, including bovine, ovine, porcine, murine, equine, and preferably human, from any source whether natural, synthetic, semi-synthetic, or recombinant.

An "allele" or "allelic sequence," as used herein, is an alternative form of the genes encoding ROC1 and ROC2. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

"Amino acid sequence," as used herein, refers to an oligopeptide, peptide, polypeptide, or protein sequence, and fragment thereof, and to naturally occurring or synthetic molecules. Fragments of ROC1 and/or ROC2 are preferably about 5 to about 15 amino acids in length and retain the biological activity or the immunological activity of ROC1 and/or ROC2. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

As used herein, the term "antibody" refers to intact molecules as well as fragments thereof, such as Fa, F(ab')2, and Fc, which are capable of binding the epitopic determinant. Antibodies that bind ROC1 and/or ROC2 polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to ROC1 and/or ROC2 or the encoded ROC1 and/or ROC2. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

The term "hybridization", as used herein, refers to any process by which a strand of nucleic acid binds with a complementary strand through base pairing. The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925

(1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al, *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English*, 30:423 (1991); Letsinger, et al., *J. Am. Chem. Soc.*, 110:4470 (1988); Letsinger, et al., Nucleoside & Nucleotide, 13:1597 (1994); Chapters 2 and 3, ASC Symposium Series 580, "Carbohydrate Modifications in Antisense Research," Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research," Ed. Y. S. Sanghui and P. Dan Cook. Nucleic acids containing one or more carbocyclic sugars are also included within the definition of nucleic acids (see Jenkins, et al., *Chem. Soc. Rev.*, (1995) pp. 169-176). Several nucleic acid analogs are described in Rawls, *C & E News*, Jun. 2, 1997, page 35. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

The term "sample", as used herein, is used in its broadest sense. A biological sample suspected of containing nucleic acid encoding ROC1 and/or ROC2, or fragments thereof, or ROC1 and/or ROC2 itself may comprise a bodily fluid, extract from a cell, chromosome, organelle, or membrane isolated from a cell, a cell, genomic DNA, RNA, or cDNA (in solution or bound to a solid support, a tissue, a tissue print, and the like). The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors may be varied to generate conditions of either low or high stringency different from, but equivalent to, the above listed conditions.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

Polynucleotides of the present invention include those coding for proteins homologous to, and having essentially the same biological properties as, the proteins disclosed herein, and particularly the DNA disclosed herein as SEQ ID NO:1 and encoding the protein ROC1 given herein SEQ ID NO:2; as well as the DNA disclosed herein as SEQ ID NO: 3 and encoding the protein ROC2 given herein as SEQ ID NO:4. This definition is intended to encompass natural allelic sequences thereof. Thus, isolated DNA or cloned genes of the present invention can be of any species of origin, including mouse, rat, rabbit, cat, porcine, and human, but are preferably of mammalian origin. Thus, polynucleotides that hybridize to DNA disclosed herein as SEQ ID NO:1 (or fragments or derivatives thereof which serve as hybridization probes as discussed below) and which code on expression for a protein of the present invention (e.g., a protein according to SEQ ID NO:2); and polynucleotides that hybridize to DNA disclosed herein as SEQ ID NO:3 (or fragments or derivatives thereof which serve as hybridization probes as discussed below) and which code on expression for a protein of the present invention (e.g., a protein according to SEQ ID NO:4), are also an aspect of the invention. Conditions which will permit other polynucleotides that code on expression for a protein of the present invention to hybridize to the DNA of SEQ ID NO:1 or SEQ ID NO: 3 disclosed herein can be determined in accordance with known techniques. For example, hybridization of such sequences may be carried out under conditions of reduced stringency, medium stringency or even stringent conditions (e.g., conditions represented by a wash stringency of 35-40% Formamide with 5× Denhardt's solution, 0.5% SDS and 1× SSPE at 37° C.; conditions represented by a wash stringency of 40-45% Formamide with 5× Denhardt's solution, 0.5% SDS, and 1× SSPE at 42° C.; and conditions represented by a wash stringency of 50% Formamide with 5× Denhardt's solution, 0.5% SDS and 1× SSPE at 42° C., respectively) to DNA of SEQ ID NO:1 or SEQ ID NO: 3 disclosed herein in a standard hybridization assay. See, e.g., J. Sambrook et al., *Molecular Cloning, A Laboratory Manual* (2d Ed. 1989) (Cold Spring Harbor Laboratory). In general, sequences which code for proteins of the present invention and which hybridize to the DNA of SEQ ID NO:1 or SEQ ID NO: 3 disclosed herein will be at least 75% homologous, 85% homologous, and even 95% homologous or more with SEQ ID NO:1 or SEQ ID NO:3, respectively. Further, polynucleotides that code for proteins of the present invention, or polynucleotides that hybridize to that as SEQ ID NO:1 or SEQ ID NO:3, but which differ in codon sequence from SEQ ID NO:1 or SEQ ID NO:3 due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

Although nucleotide sequences which encode ROC1 and/or ROC2 and its variants are preferably capable of hybridizing to the nucleotide sequence of the naturally occurring ROC1 and/or ROC2 under appropriately selected conditions of stringency, it may be advantageous to produce nucleotide sequences encoding ROC1 and/or ROC2 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding ROC1 and/or ROC2 and its derivatives without altering the encoded amino acid sequences include the production of RNA transcripts having more desirable properties, such as a greater half-life, than transcripts produced from the naturally occurring sequence.

In one embodiment of the invention, ROC nucleic acids (defined as polynucleotides encoding ROC proteins of fragments thereof), or ROC proteins (as defined above) are initially identified by substantial nucleic acid and/or amino acid sequence identity or similarity to the sequence(s) provided herein. In a preferred embodiment, ROC nucleic acids or ROC proteins have sequence identity or similarity to the sequences provided herein as described below and one or more of the ROC protein bioactivities as further described herein. Such sequence identity or similarity can be based upon the overall nucleic acid or amino acid sequence.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, *Adv. Appl. Math.* 2,482 (1981), by the sequence identity alignment algorithm of Needleman & Wunsch, *J. Mol. Biol.* 48,443 (1970), by the search for similarity method of Pearson & Lipman, *Proc. Natl. Acad. Sci. USA* 85,2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," *Macromolecule Sequencing and Synthesis*, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp CABIOS 5,151-153 (1989). Useful PILEUP parameters including a default gap weight of 3.00, a default gap length weight of 0.10, and weighted end gaps.

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266,460-480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. *Nucleic Acids Res.* 25, 3389-3402. Gapped BLAST uses BLOSUM-62 substitution scores; threshold T parameter set to 9; the two-hit method to trigger ungapped extensions; charges gap lengths of k a cost of 10+k, $X_u$ set to 16, and $X_g$ set to 40 for database search stage and to 67 for the output stage of the algorithms. Gapped alignments are triggered by a score corresponding to ~22 bits.

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of NU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequences in the Figures, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

The invention also encompasses production of DNA sequences, or fragments thereof, which encode ROC1 and/or ROC2 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding ROC1 and/or ROC2 or any fragment thereof.

Knowledge of the nucleotide sequence as disclosed herein in SEQ ID NO:1 or SEQ ID NO:3 can be used to generate hybridization probes which specifically bind to the DNA of the present invention or to mRNA to determine the presence of amplification or overexpression of the proteins of the present invention.

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

Methods for DNA sequencing which are well known and generally available in the art may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding ROC1 and/or ROC2 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) *PCR Methods Applic.* 2, 318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells are cells which have been transformed or transfected with vectors containing DNA coding for proteins of the present invention need not express protein.

Suitable host cells include prokaryotes, yeast cells, or higher eukaryotic organism cells. Prokaryote host cells include gram negative or gram positive organisms, for example *Escherichia coli* (*E. coli*) or *Bacilli*. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. See Bolivar et al., *Gene* 2, 95 (1977). Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No.36, 776) and the tac promoter (H. De Boer et al., *Proc. Natl. Acad. Sci. USA* 80, 21 (1983). The promoter and Shine-Dalgarno sequence (for prokaryotic host expression) are operably linked to the DNA of the present invention, i.e., they are positioned so as to promote transcription of the messenger RNA from the DNA.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980). The promoter and Shine-Dalgarno sequence (for prokaryotic host expression) are operably linked to the DNA encoding the desired protein, i.e., they are positioned so as to promote transcription of the protein messenger RNA from the DNA.

Eukaryotic microbes such as yeast cultures may be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977). The presence of the trp1 lesion in the yeast host cell genome then provides an effective environment for detecting transformation by growth in the absence of tryptophan.

Suitable promoting sequences in yeast vectors include the promoters for metallothionein, 3-phospho-glycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculorivus expression vector (e.g., vectors derived from *Autographa californica* MNPV, *Trichoplusia ni* MNPV, *Rachiplusia ou* MNPV, or *Galleria ou* MNPV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

In mammalian host cells, a number of viral-based expression systems may be utilized. In cases where an adenovirus is used as an expression vector, sequences encoding ROC1 and/or ROC2 may be ligated into an adenovirus transcription/translation complex consisting of the late promoter and tripartite leader sequence. Insertion in a non-essential E1 or E3 region of the viral genome may be used to obtain a viable virus which is capable of expressing ROC1 and/or ROC2 in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival or transformants in culture medium that is toxic, or from which the cells cannot obtain critical nutrition without having taken up the marker protein.

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with, Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; KGln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

As noted above, the present invention provides isolated and purified ROC1 and ROC2 proteins, such as mammalian (or more preferably human) ROC1 and ROC2. Such proteins can be purified from host cells which express the same, in accordance with known techniques, or even manufactured synthetically.

Nucleic acids of the present invention, constructs containing the same and host cells that express the encoded proteins are useful for making proteins of the present invention.

Proteins of the present invention are useful as immunogens for making antibodies as described herein, and these antibodies and proteins provide a "specific binding pair." Such specific binding pairs are useful as components of a variety of immunoassays and purification techniques, as is known in the art.

The proteins of the present invention are of known amino acid sequence as disclosed herein, and hence are useful as molecular weight markers in determining the molecular weights of proteins of unknown structure.

Specific initiation signals may also be used to achieve more efficient translation of sequences encoding ROC1 and/or ROC2. Such signals include the ATG initiation codon and adjacent sequences. In cases where sequences encoding ROC1 and/or ROC2, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and may be chosen to ensure the correct modification and processing of the foreign protein.

For long-term, high-yield production of recombinant proteins, stable expression is preferred. For example, cell lines which stably express ROC1 and/or ROC2 may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes which can be employed in tk- or aprt-cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047-51). Recently, the use of visible markers has gained popularity with such markers as anthocyanins, glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression may need to be confirmed. For example, if the sequence encoding ROC1 and/or ROC2 is inserted within a marker gene sequence, transformed cells containing sequences encoding ROC1 and/or ROC2 can be identified by the absence of marker gene function. Alternatively, a marker gene can be placed in tandem with a sequence encoding ROC1 and/or ROC2 under the control of a single promoter. Expression of the marker gene in response to induction or selection usually indicates expression of the tandem gene as well.

Alternatively, host cells which contain the nucleic acid sequence encoding ROC1 and/or ROC2 and express ROC1 and/or ROC2 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding ROC1 and/or ROC2 can be detected by DNA-DNA or DNA-RNA hybridization or amplification using probes or fragments or fragments of polynucleotides encoding ROC1 and/or ROC2. Nucleic acid amplification based assays involve the use of oligonucleotides or oligomers based on the sequences encoding ROC1 and/or ROC2 to detect transformants containing DNA or RNA encoding ROC1 and/or ROC2.

A variety of protocols for detecting and measuring the expression of ROC1 and/or ROC2, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on ROC1 and/or ROC2 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides encoding ROC1 and/or ROC2 include oligolabeling, nick translation, end-labeling or PCR amplification using a labeled nucleotide. Alternatively, the sequences encoding ROC1 and/or ROC2, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6, and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding ROC1 and/or ROC2 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode ROC1 and/or ROC2 may be designed to contain signal sequences which direct secretion of ROC1 and/or ROC2 through a prokaryotic or eukaryotic cell membrane. Other constructions may be used to join sequences encoding ROC1 and/or ROC2 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and ROC1 and/or ROC2 may be used to facilitate purification. One such expression vector provides for expression of a fusion protein containing ROC1 and/or ROC2 and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263-281) while the enterokinase cleavage site provides a means for purifying ROC1 and/or ROC2 from the fusion protein. A discussion of vectors which contain fusion proteins is provided in Kroll, D. J. et al. (1993; DNA Cell Biol. 12:441-453).

In addition to recombinant production, fragments of ROC1 and/or ROC2 may be produced by direct peptide synthesis using solid-phase techniques (Merrifield J. (1963) *J. Am. Chem. Soc.* 85, 2149-2154). Protein synthesis may be performed using manual techniques or by automation. Automated synthesis may be achieved, for example, using Applied Biosystems 431A Peptide Synthesizer (Perkin Elmer). Various fragments of ROC1 and/or ROC2 may be chemically synthesized separately and combined using chemical methods to produce the full length molecule.

Antibodies that specifically bind to the proteins of the present invention (i.e., antibodies which bind to a single antigenic site or epitope on the proteins) are useful for a variety of diagnostic purposes.

Antibodies to ROC1 and/or ROC2 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with ROC1 and/or ROC2 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to ROC1 and/or ROC2 have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of ROC1 and/or ROC2 amino acids may be fused with those of another protein such as keyhole limpet hemocyanin and antibody produced against the chimeric molecule.

Monoclonal antibodies to ROC1 and/or ROC2 may be prepared using any technique which provides for the production of antibody molecules by continuous cell lines in culture. These include, but are not limited to, the hybridoma technique, the human B-cell hybridoma technique, and the EBV-hybridoma technique. See, e.g., Kohler, G. et al. (1975) *Nature*, 256, 495-497; Kozbor, D. et al. (1985) *J. Immunol.*

Methods 81, 31-42; Cote, R. J. et al. (1983) *Proc. Natl. Acad. Sci. USA* 80, 2026-2030; Cole, S. P. et al. (1984) *Mol. Cell Biol.* 62,109-120.

In addition, techniques developed for the production of "chimeric antibodies", the splicing of mouse antibody genes to human antibody genes to obtain a molecule with appropriate antigen specificity and biological activity can be used (Morrison, S. L. et al. (1984) *Proc. Natl. Acad. Sci.* 81, 6851-6855; Neuberger, M. S. et al. (1984) *Nature* 312:604-608; Takeda, S. et al. (1985) *Nature* 314:452-454). Alternatively, techniques described for the production of single chain antibodies may be adapted, using methods known in the art, to produce ROC1 and/or ROC2-specific single chain antibodies. Antibodies with related specificity, but of distinct idiotypic composition, may be generated by chain shuffling from random combinatorial immunoglobin libraries (Burton D. R. (1991) *Proc. Natl. Acad. Sci.* 88,11120-3).

Antibodies may also be produced by inducing in vivo production in the lymphocyte population or by screening immunoglobulin libraries or panels of highly specific binding reagents as disclosed in the literature. See, e.g., Orlandi, R. et al. (1989) *Proc. Natl. Acad. Sci,* 86, 3833-3837; Winter, G. et al. (1991) *Nature* 349,:293-299.

Antibody fragments which contain specific binding sites for ROC1 and/or ROC2 may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity. See Huse, W. D. et al. (1989) *Science* 254,1275-1281.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between ROC1 and/or ROC2 and its specific antibody. A two-site, monoclonal-based immunoassay utilizing monoclonal antibodies reactive to two non-interfering ROC1 and/or ROC2 epitopes is preferred, but a competitive binding assay may also be employed (Maddox, supra).

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Kits for determining if a sample contains proteins of the present invention will include at least one reagent specific for detecting the presence or absence of the protein. Diagnostic kits for carrying out antibody assays may be produced in a number of ways. In one embodiment, the diagnostic kit comprises (a) an antibody which binds proteins of the present invention conjugated to a solid support and (b) a second antibody which binds proteins of the present invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

Assays for detecting the polynucleotides encoding ROC1 or ROC2 in a cell, or the extent of amplification thereof, typically involve, first, contacting the cells or extracts of the cells containing nucleic acids therefrom with an oligonucleotide that specifically binds to ROC1 or ROC2 polynucleotide as given herein (typically under conditions that permit access of the oligonucleotide to intracellular material), and then detecting the presence or absence of binding of the oligonucleotide thereto. Again, any suitable assay format may be employed (see, e.g., U.S. Pat. No. 4,358,535 to Falkow et al.; U.S. Pat. No. 4,302,204 to Wahl et al.; U.S. Pat. No. 4,994,373 to Stavrianopoulos et al; U.S. Pat. No. 4,486, 539 to Ranki et al.; U.S. Pat. No. 4,563,419 to Ranki et al.; and U.S. Pat. No. 4,868,104 to Kurn et al.) (the disclosures of which applicant specifically intends be incorporated herein by reference).

Antisense oligonucleotides and nucleic acids that express the same may be made in accordance with conventional techniques. See, e.g., U.S. Pat. No. 5,023,243 to Tullis; U.S. Pat. No. 5,149,797 to Pederson et al. The length of the antisense oligonucleotide (i.e., the number of nucleotides therein) is not critical so long as it binds selectively to the intended location, and can be determined in accordance with routine procedures. In general, the antisense oligonucleotide will be from 8, 10 or 12 nucleotides in length up to 20, 30, or 50 nucleotides in length. Such antisense oligonucleotides may be oligonucleotides wherein at least one, or all, or the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues may be modified as described. In another non-limiting example, such antisense oligonucleotides are oligonucleotides wherein at least one, or all, of the nucleotides contain a 2' loweralkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described. See also P. Furdon et al., *Nucleic Acids Res.* 17, 9193-9204 (1989); S. Agrawal et al., *Proc. Natl. Acad. Sci. USA* 87, 1401-1405 (1990); C. Baker et al., *Nucleic Acids Res.* 18, 3537-3543 (1990); B. Sproat et al., *Nucleic Acids Res.* 17, 3373-3386 (1989); R. Walder and J. Walder, *Proc. Natl. Acad. Sci. USA* 85, 5011-5015 (1988).

In a preferred embodiment, the ROC proteins, nucleic acids, variants, modified proteins, cells and/or transgenics containing the ROC nucleic acids or proteins are used in screening assays. Identification of the ROC proteins provided herein permits the design of drug screening assays for compounds that bind or interfere with the binding to the ROC proteins and for compounds which modulate ROC activity.

The assays described herein preferably utilize the human ROC proteins, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative ROC proteins may be used, including deletion ROC proteins as outlined above.

In a preferred embodiment, the methods comprise combining a ROC protein and a candidate bioactive agent, and determining the binding of the candidate agent to the ROC proteins. In other embodiments, further discussed below, binding interference or bioactivity is determined.

The term "candidate bioactive agent" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to alter ROC activity, may be used.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. For example, a library of all combinations of a peptide 7 to 20 amino acids in length, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. In another preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of prokaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. In another preferred embodiment, the candidate bioactive agents are organic chemical moieties, a wide variety of which are available in the literature.

In one embodiment of the methods described herein, portions of ROC proteins are utilized; in a preferred embodiment, portions having ROC activity are used. ROC activity is as described herein and includes binding activity to cullins as outlined herein. In addition, the assays described herein may utilize either isolated ROC proteins or cells comprising the ROC proteins.

Generally, in a preferred embodiment of the methods herein, for example for binding assays, the ROC proteins or the candidate agent is ron-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, TEFLON®, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block important sites on the protein when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the ROC proteins is bound to the support, and a candidate bioactive agent is added to the assay. Alternatively, the candidate agent is bound to the support and the ROC proteins are added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays, and the like.

The determination of the binding of the candidate bioactive agent to the ROC proteins may be done in a number of ways. In a preferred embodiment, the candidate bioactive agent is labelled, and binding determined directly. For example, this may be done by attaching all or a portion of the ROC proteins to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. ROC proteins), such as an antibody, peptide, binding partner, ligand, etc. In a preferred embodiment, the competitor is a cullin. Under certain circumstances, there may be competitive binding as between the bioactive agent and the binding moiety, with the binding moiety displacing the bioactive agent. This assay can be used to determine candidate agents which interfere with binding between ROC proteins and its biological binding partners. "Interference of binding" as used herein means that native binding of the ROC proteins differs in the presence of the candidate agent. The binding can be eliminated or can be with a reduced affinity. Therefore, in one embodiment, interference is caused by, for example, a conformation change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40□ C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the ROC proteins and thus is capable of binding to, and potentially modulating, the activity of the ROC proteins. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the ROC proteins with a higher affinity. Thus, if the candidate bioactive agent is labeled, the presence of the label on the support, coupled with a lack of competitor binding, may indicate that the candidate agent is capable of binding to the ROC proteins.

In a preferred embodiment, the methods comprise differential screening to identity bioactive agents that are capable of modulating the activity of the ROC proteins. Such assays can be done with the ROC proteins or cells comprising said ROC proteins. In one embodiment, the methods comprise combining an ROC proteins and a competitor in a first sample. A second sample comprises a candidate bioactive agent, an ROC proteins and a competitor. The binding of the competitor is determined for both samples, and a change, or difference in binding between the two samples indicates the presence of an agent capable of binding to the ROC proteins and potentially modulating its activity. That is, if the binding of the competitor is different in the second sample relative to the first sample, the agent is capable of binding to the ROC proteins.

Alternatively, a preferred embodiment utilizes differential screening to identify drug candidates that bind to the native ROC proteins, but cannot bind to modified ROC proteins. The structure of the ROC proteins may be modeled, and used in rational drug design to synthesize agents that interact with that site. Drug candidates that affect cell cycle bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of the ROC proteins may also be done. In a preferred embodiment, methods for screening for a bioactive agent capable of modulating the activity of ROC proteins comprise the steps of adding a candidate bioactive agent to a sample of a ROC proteins (or cells comprising a ROC proteins) and determining an alteration in the biological activity of the ROC proteins. "Modulating the activity of a ROC proteins" includes an increase in activity, a decrease in activity, or a change in the type or kind of activity present. Thus, in this embodiment, the candidate agent should both bind to the ROC protein (although this may not be necessary), and alter its biological or biochemical activity as defined herein. The methods include both in vitro screening methods, as are generally outlined above, and in vivo screening of cells for alterations in the presence, distribution, activity or amount of ROC proteins.

Thus, in this embodiment, the methods comprise combining a ROC protein and a candidate bioactive agent, and evaluating the effect on the bioactivity of the ROC proteins. By "ROC protein activity" or grammatical equivalents herein is meant at least one of the ROC proteins' biological activities, including, but not limited to, the proteins' ability to bind cullins (including, but not limited to, cullin 1, 2, 3, 4A and 5), its activity in ligating ubiquitin and the ubiquitin-dependent proteolytic process, its role in SICp degradation, and any other activity of ROC proteins as described herein, etc.

In a preferred embodiment, the activity of the ROC proteins is decreased; in another preferred embodiment, the activity of the ROC proteins is increased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of an ROC proteins. The methods comprise adding a candidate bioactive agent, as defined above, to a cell comprising ROC proteins. Preferred cell types include almost any cell. The cells contain a recombinant nucleic acid that encodes a ROC protein. In a preferred embodiment, a library of candidate agents are tested on a plurality of cells.

Detection of ROC activity may be done as will be appreciated by those in the art. There are a number of parameters that may be evaluated or assayed to allow the detection of alterations in ROC bioactivity.

The measurements can be determined wherein all of the conditions are the same for each measurement, or under various conditions, with or without bioactive agents, etc. For example, measurements of ROC activity can be determined in a cell or cell population wherein a candidate bioactive agent is present and wherein the candidate bioactive agent is absent.

In another example, the measurements of ROC activity are determined wherein the condition or environment of the cell or populations of cells differ from one another. For example, the cells may be evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts).

By a "population of cells" or "library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines. In a preferred embodiment, cells that are replicating or proliferating are used; this may allow the use of retroviral vectors for the introduction of candidate bioactive agents. Alternatively, non-replicating cells may be used, and other vectors (such as adenovirus and lentivirus vectors) can be used. In addition, although not required, the cells are compatible with dyes and antibodies.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc.

The proteins and nucleic acids provided herein can also be used for screening purposes wherein the protein-protein interactions of the ROC proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340, 245 (1989); Vasavada et al., Proc. Natl. Acad. Sci. USA 88, 10686 (1991); Fearon et al., Proc. Natl. Acad. Sci. USA 89, 7958 (1992); Dang et al., Mol. Cell. Biol. 11, 954 (1991); Chien et al., Proc. Natl. Acad. Sci. USA 88, 9578 (1991); and U.S. Pat. Nos. 5,283,173, 5,667, 973, 5,468,614, 5,525,490, and 5,637,463.

In general, two nucleic acids are transformed into a cell, where one is a "bait" such as the gene encoding a ROC proteins or a portion thereof, and the other encodes a test candidate. Only if the two expression products bind to one another will an indicator, such as a fluorescent protein, be expressed. Expression of the indicator indicates when a test candidate binds to the ROC proteins. Using the same system and the newly-identified proteins the reverse can be performed. Namely, the ROC proteins provided herein can be used to identify new baits, or agents which interact with ROC proteins. Additionally, the two-hybrid system can be used wherein a test candidate is added in addition to the bait and the ROC proteins encoding nucleic acids to determine agents which interfere with the bait, such as cullins.

In this way, bioactive agents are identified. Bioactive agents (i.e., compounds) with pharmacological activity are those compounds that are able to enhance or interfere with the activity of at least one of the ROC proteins. The compounds having the desired pharmacological activity may be administered in a pharmaceutically acceptable carrier (i.e., a pharmaceutical formulation) to a host or subject. Suitable subjects are preferably human subjects, but may also be other mammalian subjects, such as dogs, cats and livestock (i.e., for veterinary purposes).

Pharmaceutical formulations of the present invention comprise compounds with pharmacological activity (as identified using methods of the present invention) in a pharmaceutically acceptable carrier. Suitable pharmaceutical formulations include those suitable for inhalation, oral, rectal, topical, (including buccal, sublingual, dermal, vaginal and intraocular), parenteral (including subcutaneous, intradermal, intramuscular, intravenous and intraarticular) and transdermal administration. The compositions may conveniently be presented in unit dosage form and may be prepared by any of the methods well known in the art. The most suitable route of administration in any given case may depend upon the anatomic location of the condition being treated in the subject, the nature and severity of the condition being treated, and the particular pharmacologically active compound which is being used. The formulations may conveniently be presented in unit dosage form and may be prepared by any of the methods well known in the art.

In the manufacture of a medicament according to the invention (the "formulation"), pharmacologically active compounds or the physiologically acceptable salts thereof (the "active compounds") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 99% by weight of the active compound. One or more active compounds may be incorporated in the formulations of the invention, which formulations may be prepared by any of the well known techniques of pharmacy consisting essentially of admixing the components, optionally including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, e.g., *Pharmaceutical Research* 3, 318 (1986)) and typically take the form of an optionally buffered aqueous solution of the active compound.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the pharmaceutically active compounds identified with the methods described herein may be lyophilized to produce a lyophilizate which may be reconstituted with a pharmaceutically acceptable carrier, such as water, to regenerate a liposomal suspension.

Other pharmaceutical formulations may be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines, and lecithin.

In addition to the pharmacologically active compounds, the pharmaceutical formulations may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical formulations of the present invention may be lyophilized using techniques well known in the art.

The therapeutically effective dosage of any specific pharmacologically active compound identified by methods of the invention, the use of which compounds is in the scope of present invention, will vary somewhat from compound to compound, and subject to subject, and will depend upon the condition of the patient and the route of delivery.

The following Examples are provided to illustrate the present invention, and should not be construed as limiting thereof.

EXAMPLE 1

Materials and Methods cDNA Clones, Plasmids Constructs and Yeast Two Hybrid Assay A cDNA sequence encoding full-length mouse cullin 4A was used as a bait to screen a HeLa cell derived cDNA library for cullin-interacting proteins by the yeast two-hybrid assay described in Michel and Xiong, Cell Growth. Differ. 9, 439-445 (1998). The full length cDNA clones for both human ROC2 and APC11 were isolated by PCR amplification from a HeLa cDNA library and confirmed by DNA sequencing. To identify cDNA clones encoding the full length mammalian APC2, the EST database was searched. Full length cDNA clones were not available for human APC2 in the present EST database. Instead, a near full-length mouse APC2 EST cDNA clone (W13204) was identified that predicts a 823 amino acid open reading frame with a calculated molecular weight of 94 kDa. This mouse cDNA clone is one amino acid residue longer than the published human APC2 (Yu et al., 1998a), but is missing the initiation methionine codon. Given the extremely close relatedness between mouse and human APC2 proteins (93% identity over the entire 823 residues), the mouse APC2 was used when testing for the interaction with human APC11.

Yeast cDNA sequences were amplified from yeast genomic DNA by PCR and verified by DNA sequencing. The primers used for ScROC1 were: 5'-TTT AAA GAG AAA TA GGATCCC ATG AGC AAC GAA-3' [SEQ ID NO: 5] and 5'-TTA AAT GTT TAC GGG GAATTC ATT TTT TCA CCT-3' [SEQ ID NO: 6] incorporating a 5' BamHI site and a 3' EcoRI site (underlined) by which the PCR product was inserted in frame into the pGAD prey vector. pGBT8-ScROC1 was constructed using SmaI and SacI restriction sites from pGEX-ScROC1. Primers for amplifying ScAPC11 are: 5'-GGC AAT ACA GAT TAGGATCCT ATG AAA GTT AAA-3'[SEQ ID NO: 7] and 5'-AAT TGT GAT TTC TA GAATTCT TTT TTA TCG TAA-3' [SEQ ID NO: 8] incorporating a 5' BamHI site and a 3' EcoRI site (underlined) by which the PCR product was inserted in frame into the pGAD vector. CDC53 was provided by Dr. Mike Tyers and was subcloned from pMT1144 into pBSKS using BamHI and NotI sites. From here it was subcloned in frame into pGBT8 using BamHI and SacI sites to create pGBT8-CDC53. CUL B (ORF YGR003w) was PCR cloned using primers: 5'-ATC CC CATGGCT ATG ATA ACT AAT AAG AAA ATA-3' [SEQ ID NO: 9] and 5'-CTG CAGAGCTCG TTA GGA AAG GTA ATG GTA ATA-3' [SEQ ID NO: 10] incorporating a 5' NcoI site and a 3' SacI site (underlined) by which the PCR product was inserted in frame into the pGBT8 bait vector. CUL C (ORF YJL047c) was PCR cloned using primers: 5'-ATC CC CATGGCT ATG ATA AAT GAG AGC GTT TCC-3' [SEQ ID NO: 11] and 5'-AGC TCGTCGACA TTA GTA CTT GTA AGT TGC TAT-3' [SEQ ID NO: 12] incorporating a 5' NcoI site and a 3' SalI site (underlined) by which the PCR product was inserted in frame into the pGBT8 bait vector. ScAPC2 was PCR cloned using primers: 5'-ATC CCCATGGCT ATG TCA TTT CAG ATT ACC CCA-3'[SEQ ID NO: 13] and 5'-AGC TCGTCGACA TCA TGA GTT TTT ATG CCC ATT-3' [SEQ ID NO: 14] incorporating a 5' NcoI site and a 3' SalI site (underlined) by which the PCR product was inserted in frame into the pGBT8 bait vector. All PCR clonings were done using lyticase treated YEF473 genomic DNA as template using the following protocol: 1 min 94° C., 1 min 55° C., 1 min/kb 68° C. for 25 cycles followed by a 10 min extension at 68° C. For ScROC1 and ScAPC11, Pfu proofreading DNA polymerase (Stratagene) was used in reactions containing 1× PCR buffer, 2.5 mM $MgCl_2$, 0.5 mM each primer and 0.1 mM dNTPs. For PCR amplification of CUL B, CUL C and ScAPC2, the long template Expand kit (Boehringer Mannheim) was used following manufacturer's instructions. Reactions contained 0.1 mM $MgCl_2$ (Buffer 1), 0.2 mM dNTPs, 0.5 mM each primer and 0.1 mg/ml BSA. ScROC1, ScAPC11, hROC1 and hROC2 were all inserted into the p414-ADH vector (CEN) using 5' BamHI and 3' XhoI restriction sites.

For expression in mammalian cells, individual cDNA clones were subcloned into the pcDNA3 vector under the control of CMV promoter (Invitrogen), pcDNA3-HA or pcDNA3-Myc, for expressing HA or myc epitope tagged fusion protein. For the yeast two-hybrid assay, individual cullin sequences were cloned into pGBT8, a modified version of pGBT9, in frame with the DNA-binding domain of Gal4. ROC1, ROC2 and APC11 were cloned into pGAD in-frame with the DNA activation domain of Gal4. Yeast two-hybrid expression plasmids for human CUL1, CUL1 deletion mutants and SKP1 were previously described (Michel and Xiong, 1998, supra).

EXAMPLE 2

Materials and Methods

Cell Lines, Culture Conditions and Cell Transfection

All mammalian cells were cultured in DMEM, supplemented with 10% FBS in a 37° C. incubator with 5% $CO_2$, which include HeLa (human cervix epithelioid carcinoma), Saos-2 (osteosarcoma), and 293T (human transformed primary embryonal kidney c cells). Cell transfections were carried out using the LipofectAMINE reagent according to the manufacturer's instructions (Gibco-BRL). For each transfection, 4 µg of total plasmid DNA (adjusted with pcDNA3 vector DNAs) was used for 60 mm dish.

EXAMPLE 3

Materials and Methods

Antibodies and Immunochemistry Procedures

Procedures for [$^{35}$S]-methionine metabolic labeling, immunoprecipitation and immunoblotting have been described previously (Jenkins, C. W. and Xiong, Y. (1995), "Immunoprecipitation and immunoblotting in cell cycle studies" in *Cell Cycle: Material and methods*, M. Pagano, ed. (New York: Springer-Verlag), pp. 250-263). The sequence of synthetic peptides used in generating rabbit polyclonal antibodies are as follows: anti-human ROC1N (CMAAAMDVDTPSGTN, amino acid residues 1-14 [SEQ ID NO:15], anti-human ROC1C (CDNREWEFQKYGH, residues 97-108 [SEQ ID NO: 16], anti-human APC11 (CRQEWKFKE, residues 76-84) [SEQ ID NO: 17], and anti-human CUL2 [CRSQASADEYSYVA, residues 733-745 [SEQ ID NO: 18]. See Kipreos et al., 1996, supra; Michel and Xiong, 1998, supra. A cysteine (underlined) was added to the N-terminus of each peptide for covalent coupling of the peptide to activated keyhole limpet haemocyanin (KLH). Antibodies to human CUL1 and SKP1 were previously described (Michel and Xiong, 1998, supra). All rabbit polyclonal antibodies used in this study were affinity purified using respective peptide columns following the manufacturer's instruction (Sulfolink Kit, Pierce, Rockford, Ill.). Monoclonal anti-HA (12CA5, Boehringer-Mannheim) and anti-myc (9E10, NeoMarker) antibodies were purchased commercially. Antibody to yeast actin was provided by Dr. J. Pringle. Coupled in vitro transcription and translation reactions were performed using the TNT kit following the manufacturer's instructions (Promega).

EXAMPLE 4

Materials and Methods

Immunopurification of ROC1 Complexes and Protein Microsequencing

For preparative scale immunopurification of ROC1 complexes, total lysate was prepared from the HeLa cells pooled from ten 150 mm plates after lysis with the NP-40 lysis buffer and clarified by high speed centrifugation (13,000 g for 30 minutes). Following pre-clearing with uncoated sephadex beads, 100 µg of affinity purified antibodies to human ROC1 was added to the clarified cell lysate. After incubating at 4° C. with rotation for 1 hour, protein A beads were added to the lysate and incubated for 1 hour. The beads were washed three times with NP-40 lysis buffer, boiled for 3 minutes in Laemmli loading buffer, and the proteins were separated by SDS-PAGE. After silver staining, ROC1-specific associated bands were identified by comparing with a parallel immunoprecipitation of the same HeLa lysate with the same anti-ROC1 antibody in the presence of molar excess of competing antigen peptide. Competable bands at molecular weight between 70 to 120 kDa were excised from the SDS gel and subjected to in-gel protease digestion using lysylendopeptidase (50 ng/ml). Digested peptide fragments was extracted by acetonitrile and separated by reverse-phase high pressure liquid chromatography on a Hewlett Packard 1100 HPLC system using a C18 column (1 mm×250 mm, Vydac). Protein sequences of individual peptides collected from HPLC were determined on an automated ABI microsequencer at Glaxo-Wellcome protein microsequencing facility.

EXAMPLE 5

Materials and Methods

Yeast Strains

All *S. cerevisiae* strains were derived from YEF473 (a/α0 ura3-52/ura3-52 his3Δ-200/his3Δ-200 trp1Δ-63/trp1Δ-63 leu2Δ-1/leu2Δ-1 lys2-801/lys2-801). Yeasts were cultured at 30° C. unless otherwise indicated in YP medium or SD medium (lacking appropriate amino acids) containing 2% glucose or 2% raffinose plus varying amounts of galactose, as appropriate. To determine protein expression, yeast cultures were collected by centrifugation, washed once with distill water and stored at −80° C. overnight. Cell pellets were resuspended in lysis buffer containing 50 mM Tris-HCl, pH 7.5, 50 mM NaCl, 0.2% Triton X-100, 1 mM DTT, 1 mM PMSF, 1 mM $NaVO_3$ and 1× protease inhibitors (25 µ/ml leupeptin, 25 µ/ml aprotonin, 1 mM benzamidine and 10 µ/ml tyrpsin inhibitor). Glass beads were added, and samples were vortexed 4×30 sec with at least 30 sec on ice between each vortex. Suspension was transferred to a new Eppendorf tube and centrifuged at 13000 g at 4° C. for 30 min. Protein concentration in the whole cell extract were measured using Bradford assay and equal amount of total protein from each sample was separated by SDS-PAGE and followed by immunoblotting. For nuclei staining, yeast was fixed in 3.7% formaldehyde in culturing medium for 1 hr. in a roller drum at 30° C. Fixed cells were washed 3 times in 1× PBS and resuspended in mounting medium (1% w/v p-phenylenediamine (Sigma) in 1× PBS pH 9, 90% glycerol and 0.5 µg/ml Hoechst 33258 dye) as described in Pringle, J. R. et al., (1991), "Immunofluorescence methods for yeast" in *Methods in Enzymol*. 194, 565-602.

Mutant yeast strains were constructed using PCR-based gene deletion and modification by homologous recombination according to Longtine et al., *Yeast* 14(10), 953-961 (1998). Primers for PCR products for all strains constructed were designed based on the sequences published in the database and contained 40 bp of sequence homologous to the gene specific sequence (upper case) and 20 bp homologous to the vector template (lower case). To create a perfect deletion of ROC1 and replace it with a module containing the *E. coli* kanr gene (strain JM1), pFA6a-kanMX6 template was used with primers ROC1-F1 (5'-TTCTCCAGTGGCAGAGAACTT-TAAAGAGAAATAGTTCAACcggatccccgggttaattaa 5') [SEQ ID NO: 19] and ROC1-R1 (5'-ACCTCGGTATGATT-TAAATGTTTACGGGCAAT-TCATTTTTgaattcgagctcgtttaaac 3') [SEQ ID NO: 20]. To integrate chromosomally the *S. pombe* his5+ gene followed by the GAL1 promoter and an HA3 tag in frame with the ScROC1 gene (strain JM5), pFA6a-His3MX6-pGAL1-HA3 template was used with primers ROC1-F4 (5'ATAGACG-TATGGGCTTCAATATGTGCAATGTTGGT-TGCTAgaattcgagctcgtttaaac-3') [SEQ ID NO: 21] and ROC1-R3 (5' CATCTTCATCAACATCCATCCTGT-CAACTTCGTTGCTCATgcactgagcagcgtaat-ctg3') [SEQ ID NO: 22]. To epitope tag the C-terminus of SIC1 with HA3 tag followed by the TRP1 selectable marker (strain JM7), pFA6a-HA3-TRP1 template was used with primers SIC1-F2 (5'CAAGCCAAAGGCATTGTTTCAATCTAGG-GATCAAGAGCATcggatccccgggttaattaa 3') [SEQ ID NO: 23] and SIC1-R1 (5'TAAAATATAATCGTTCCA-GAAACTTTTTTTTTTCATTTCTgaattcgagctcgtttaaac 3')[SEQ ID NO: 24]

PCR was performed using the Expand Long Template PCR System (Boehringer Mannheim) with the following protocol. Mix 1 (25 µl) contained 2.5 µl Expand Buffer 1, 0.8 mM dNTPs, 10 µg BSA and 2 mM each primer. Mix 2 (100 µl) contained 7.5 µg Expand Buffer 1, 0.75 µL Expand enzyme mixture, and 0.1 µg template DNA. The two mixes were added together, mixed well and immediately subjected to PCR: 20 cycles of 1 min 94° C., 1 min 55° C., 1 min/kb 68° C. followed by a 10 min extension at 68° C. PCR products from at least eight reactions were pooled, extracted once with phenol:chloroform: isoamyl alcohol (25:24:1) and ethanol precipitated. PCR products were transformed into diploid YEF473 yeast (to construct strains JM1 and JM5) or into the haploid strain JM5 (to construct strain JM7) using a standard protocol and plated onto rich medium (YPD plates for strains JM1 and JM5, and YP plates plus 2% raffinose and 2% galactose for strain JM7) for two days. Plates were then replica plated onto appropriate selectable medium for 2-3 days. Selected transformants were streaked onto selectable medium twice. To identify transformants that had integrated by homologous recombination, PCR was performed on genomic DNA prepared by lyticase treatment using one primer that annealed to the module integrated and one primer that annealed to a region outside of that altered by the recombination. PCR product of the appropriate size confirmed homologous recombination. In addition, 2:2 segregation of the selectable marker also confirmed homologous recombination.

EXAMPLE 6

Materials and Methods

Ubiquitin Ligase Activity Assay

The detailed procedures for the purification of human E1 and mouse E2 CDC34, the preparation of 32P-labeled ubiquitin, as well as immuno-purification of the ROC1/CUL1 containing E3 ligase complex from transiently transfected 293T cells (FIG. 6) is described in an accompanying paper (Tan et al.). For immunoprecipitation from un-transfected cells, 2 µg of affinity-purified anti-ROC1C, anti-CUL1, or anti-APC11 was used. The immuno-purified ROC1/CUL1 containing complex immobilized on protein A agarose beads was added to an ubiquitin ligation reaction mixture (30 µl) that contained 50 mM Tris-HCl, pH 7.4, 5 mM $MgCl_2$, 2 mM NaF, 10 nM Okadaic Acid, 2 mM ATP, 0.6 mM DTT, 1 µg 32P-Ub, 60 ng E1 and 300 ng mouse CDC34 protein. The incubation was at 37° C. for 30 min unless otherwise specified herein. The reaction mixture was then added to 20 µl 4× Laemmli loading buffer with 10 mM DDT, and boiled for 3 min prior to 7.5% SDS-PAGE analysis.

EXAMPLE 7

ROC1 Interacts Directly with All Cullins

Figure 1A:
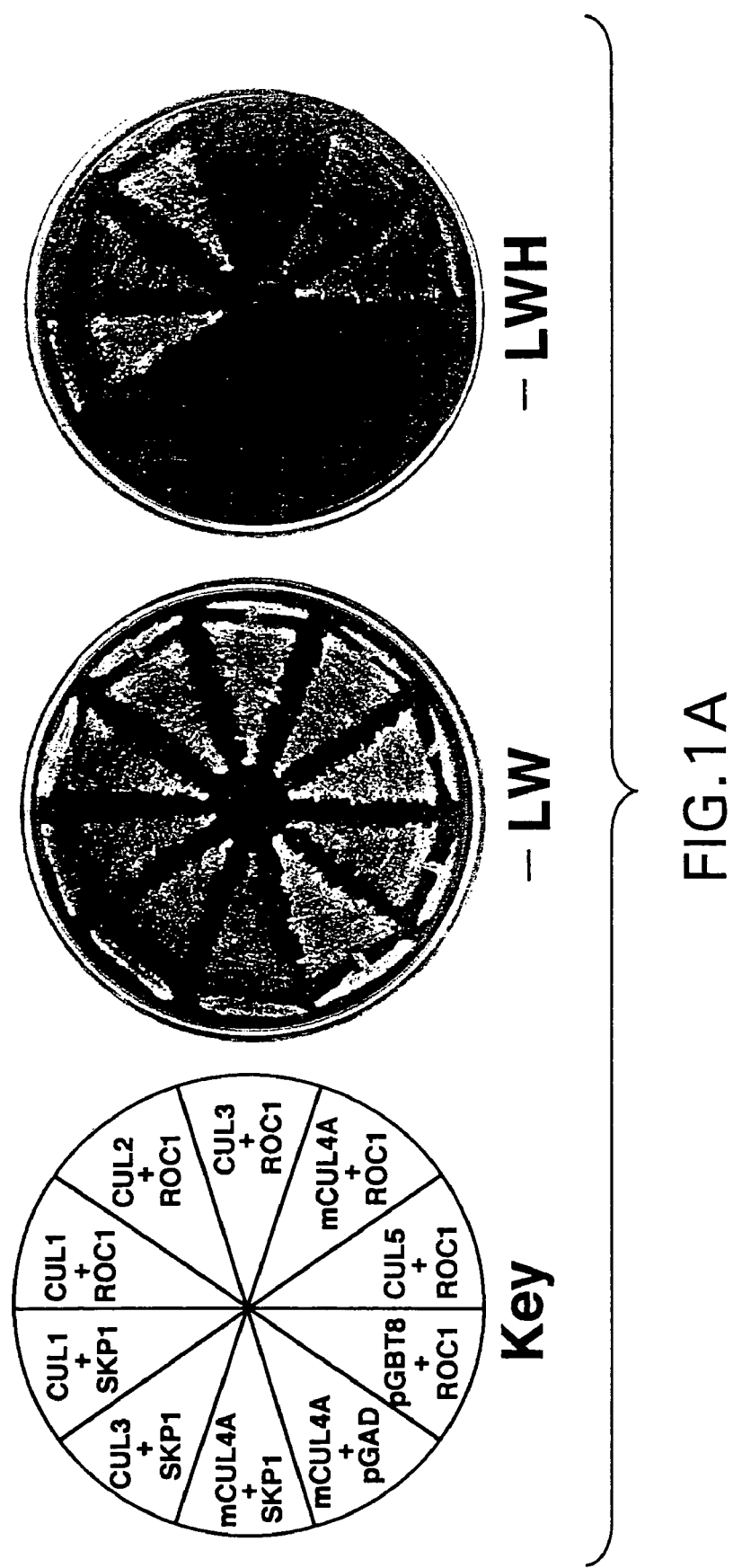

Using the yeast two-hybrid screen for cellular proteins that interact with the cullin family of proteins, as described above, a human HeLa cDNA library was screened using mouse cullin 4A as a bait. Full length mouse CUL4A encodes a 759 amino acid protein and shares 96% identity with human CUL4A that was recently identified as a candidate 13q amplicon target gene and was amplified or overexpressed in high percentage of breast cancer samples (Chen et al., 1998, supra). An estimated $3 \times 10^6$ transformants were screened. Of 17 clones isolated from this screen that grew on histidine deficient selective medium, 11 corresponded to the gene, named ROC1 (regulator of cullins), as determined by DNA sequencing and diagnostic restriction digestion analysis. The DNA sequence of ROC1 is provided herein in FIG. 2A as SEQ ID NO:1. In addition to CUL4A, ROC1 can also interact with cullin 1,2 and 5 as determined by the yeast two-hybrid assay (FIG. 1A). Cullin 3 which interacts with ROC1 very weakly in yeast cells was later found to also bind to ROC1 in cultured mammalian cells (see below). Thus, ROC1, unlike SKP1 which selectively interacts with CUL1 only (cf. Michel and Xiong, 1998, supra, FIG. 1A), appears to be a general cullin-interacting protein.

The mammalian cullin genes encode a family of closely related proteins with molecular weights of approximately 90 kDa. CUL1 interacts with SKP1 via an $NH_2$-terminal domain (see Michel and Xiong, 1998, supra). To determine the structural basis underlying the specific interaction between cullins and ROC1, the region of CUL1 required for its interaction with ROC1 was mapped. A series of CUL1 deletions from both amino- and carboxyl-terminals fused in-frame with the yeast Gal4 DNA binding domain were tested for their abilities to interact with ROC1 in yeast cells. ROC1 interacts with the C-terminal 527 amino acid residues of CUL1, but not the N-terminal 249 residues of CUL1 (FIG. 1B). In contrast, SKP1 binds to the N-terminal domain of CUL1. These results indicate that CUL1 contains at least two distinct domains, an N-terminal domain for interacting with SKP1 and a C-terminal domain for binding with ROC1. Such structural separation suggests that ROC1 is unlikely to interact with CUL1 in a competing manner with SKP1. Hence, ROC1 and SKP1 may co-exist in the same protein complex with CUL1 to perform different functions.

EXAMPLE 8

ROC1 Represents a Family of RING Finger Proteins Related to APC11

ROC1 encodes a 108 amino acid residue protein with a predicted molecular weight of 12265 D (FIG. 2A, SEQ ID NO: 2). Database searches identified ROC1 as a highly evolutionarily conserved gene whose S. cerevisiae (ROC1-Se), S. pombe (ROC1-Sp) and plant (ROC1-At) homologues share 67%, 88% and remarkably 98% protein sequence identity with human ROC1, respectively, over the 82 amino acid region compared (FIG. 2B). Database searches have also identified two additional genes, ROC2 in higher eukaryotes and APC11 in all eukaryotic species, that are closely related to ROC1. Human ROC2 and APC11 encode a 113 amino acid (SEQ ID NO:4) and an 84 residue (Mr. 9805 D) protein, respectively. The DNA sequence of ROC2 is provided herein as SEQ ID NO:3; its amino acid sequence is provided herein as SEQ ID NO:4. ROC1 and ROC2 share an overall protein sequence identity of 51% with each other and 38% and 35% identity with APC11, respectively, indicating that ROC1 and ROC2 are more closely related to each other than to APC11. Like ROC1, both ROC2 and APC11 are also highly conserved during evolution. Therefore, ROC1/ROC2/APC11 define a new family of proteins that are likely to carry out important cellular functions.

ROC/APC11 proteins contain two characteristic features: a RING finger and richness in tryptophan residues. The RING finger domain has been found in many eukaryotic proteins with diverse functions and is thought to mediate protein-protein interactions (Borden, K. L. and Freemont, P. S. (1996), *Current Opinion in Structural Biology* 6, 395-401). The majority of RING finger proteins contain a highly conserved structural motif with a histidine residue flanked by three and four cysteine residues on either side ($C_3HC_4$). Notably, the ROC1 protein from all species has a substitution of the last cysteine with an aspartic acid residue (FIG. 2B). The second feature of this family of proteins is six highly conserved tryptophan residues. Three tryptophan residues in ROC1 are followed by an acidic amino acid residue (Asn, Glu or Asp) that resemble the WD repeat and may potentially also be involved in mediating protein-protein interactions.

APC11 was recently identified as a subunit of the yeast APC complex whose loss of function resulted in a defect in the onset of anaphase and exit from mitosis (Zachariae et al., 1998, supra). Another APC subunit, APC2, was found to contain limited sequence similarity to the C-terminal region of cullins. Id. Although Applicant does not wish to be bound to any theory of the invention, these observations, together with the finding that both ROC1 and ROC2 (see below) directly interact with cullins, suggest (1) that APC11 may directly interact with APC2, (2) that the region for interacting with ROC and APC11 may be located in the conserved C-terminal portion in cullin and APC2 proteins, and (3) that ROC proteins may function in regulating ubiquitin-dependent proteolysis.

EXAMPLE 9

In vivo Association of ROC1 and Cullins

To confirm the interaction between ROC1 and cullin proteins, Saos-2 cells were transfected with plasmids directing the expression of HA-epitope tagged human ROC1 (HA-ROC1) together with CUL1 or other individual myc-epitope tagged cullins, as set forth above. Transfected cells were metabolically labeled with [$^{35}$S]-methionine, and cell lysates were immunoprecipitated reciprocally with either anti-HA, anti-CUL1 or anti-myc antibody (FIG. 3A). Neither the myc antibody cross-reacted with ROC1 (e.g., lanes 2 and 3, FIG. 3A) nor the HA antibody cross-reacted with the cullins (lane 12, FIG. 3A, and also lanes 6-9 of FIG. 4D). All five cullins were co-precipitated with ROC1 by the HA antibody. In the reciprocal immunoprecipitations, HA-ROC1 protein was detected readily in anti-myc-mCUL4A by the myc antibody, but was not evident in anti-myc-cullin 2, 3 and 5 immunocomplexes. Un-tagged CUL1 formed a complex with co-transfected ROC1 with similar efficiency as myc tagged cullins (lane 1, FIG. 3A), excluding the possibility of any artifactual binding between ROC1 and cullin proteins that might be caused by myc epitope tagging or cross-reactivity of the myc antibody. In addition to the ROC1-cullin association, several cellular proteins of unknown identity were precipitated with either ROC1 or a cullin protein, including an 130 kDa cellular protein (p130) that was co-precipitated with HA-ROC1 when CUL1, but not other cullins, was co-expressed (FIG. 3A, lane 7). The ROC1-cullins association in transfected cells has been confirmed by sequential immunoprecipitation and immunoblotting (IP-Western). Cullins 1, 2, 4A and 5 were readily detected in the anti-HA immunocomplex (data not shown)

To obtain evidence for in vivo ROC1-cullin association under more physiological conditions, rabbit polyclonal antibodies specific to ROC1 were raised. This antibody is capable of precipitating both ROC1 and the ROC1-CUL1 complex as determined by the use of in vitro translated proteins (lanes 1 and 2, FIG. 3B). From metabolically labeled HeLa and Saos-2 cells, the anti-ROC1 antibody precipitated a protein of approximately 14 kDa (lanes 3 and 5). This 14 kDa protein corresponds to ROC1 as judged by its co-migration with in vitro produced ROC1 and by competition using the antigen peptide (lanes 4 and 6). In addition to ROC1, a number of cellular proteins between 75 to 200 kDa were co-precipitated with ROC1. The presence of these proteins in the anti-ROC1 immunocomplex is blocked by the competing antigen peptide, suggesting that these proteins may specifically associate with ROC1.

This observation suggests that in vivo ROC1 may be associated with many different proteins, a conclusion consistent with its broad interaction with all cullin proteins. To directly confirm this, several proteins at molecular weights between 70 to 120 kDa were immunopurified from the ROC1 immunocomplexes (indicated as "cullins" in the FIG. 3B) and their sequences determined by protein microsequencing. At least four cullin proteins were identified from this analysis thus far; cullin 1 or cullin 2 (KDVFQK, [SEQ ID NO: 25] corresponding to residues 459-464 in human CUL1, database accession AF062536, or 428-433 of human CUL2, accession Q13617), cullin 2 (KIFLENHVRHLH, [SEQ ID NO: 26] residues 62-73, accession Q13617), cullin 3 (KDVFERYY, residues 425-432 [SEQ ID NO: 27]and KVYTYVA, [SEQ ID NO: 28] residues 762-768, accession AF062537), and cullin 4A or 4B (KRIESLIDRDY, [SEQ ID NO: 29] residues 396-406 in human CUL4A, accession Q13619 or residues 263-273 in human CUL4B, accession Q13620). The association between ROC1 with many of these cullins was not disrupted by the wash of immunocomplexes with a buffer containing 0.1% SDS (data not shown), indicating that the ROC1-cullins association is quite stable.

To further demonstrate the in vivo ROC1-cullins association without overexpression, HeLa cell lysate was immunoprecipitated with antibodies to ROC1, CUL1, and CUL2, and the precipitates analyzed by Western blotting. As shown in FIG. 3C, both CUL1 (lane 3) and CUL2 (lane 7) were readily detected in the ROC1 immunocomplexes and were specifically blocked by the competing ROC1 antigen peptide. Reciprocally, ROC1 was detected in both CUL1 (lane 1) and CUL2 (lane 5) complexes (lower panel, FIG. 3C). Demonstration of association between ROC1 and other cullins by IP-Western was not carried out because of the lack of antibodies to other cullins at present.

EXAMPLE 10

Selective Interaction Between ROC2, APC11 and Cullin Family Proteins

The yeast two-hybrid assay and in vivo binding assay described herein were used to determine whether ROC2 and APC11, like ROC1, also interact with cullins. Full length human ROC2 or APC11 was fused in-frame with the yeast Gal4 DNA activation domain and co-transformed into yeast cells with individual cullins fused to the Gal4 DNA binding domain. Almost identical to ROC1, ROC2 interacted strongly with cullins 1, 2, 4A and 5 (FIG. 4A), indicating that ROC2 is also a general cullin-interacting protein. In contrast, APC11 only interacted with cullin 5, but not other cullins (FIG. 4B).

To further asses the interaction between ROC2 and APC11 with cullins, Saos-2 cells were transfected with plasmids directing the expression of HA tagged human ROC2 (HA-ROC2) or APC11 (HA-APC11) together with untagged CUL1 or individual myc tagged cullins. Transfected cells were metabolically labeled with [$^{35}$S]-methionine, and cell lysates were immunoprecipitated with either anti-HA, anti-CUL1 or anti-myc antibody (FIGS. 4C and 4D). Transfected HA-ROC2 protein migrates as a doublet (lanes 6 to 10, FIG. 4C). The myc antibody does not cross-react with either form of ROC2 (e.g. comparing lanes 5 and 6). All five cullins were co-precipitated with ROC2 by the HA antibody (lanes 6 to 10). Reciprocally, ROC2 (preferentially the faster migrating form) was also detected in cullin 2, 3 and 4 immunocomplexes (lanes 2 to 4).

In contrast and with the exception of cullin 5, APC11 and cullins were not detected to interact with each other in reciprocal precipitations (lane 1 to 10, FIG. 4D). Cullin 5 was weakly, but reproducibly, detected in the APC11 immunocomplex (lane 10). Of all six mammalian cullins, CUL5 is the most divergent member of the cullin family and contains the highest sequence similarity to APC2. In addition to the cullins, several cellular proteins including a band of approximately 130 kDa was detected in the ROC2 complex when CUL5, but not other cullins, was co-expressed (FIG. 4C, lanes 5 and 10). p130 was not detected in cells co-transfected with CUL5 and ROC1 (lane 11 of FIG. 3A) or APC11 (lane 10 of FIG. 4D). Whether this ROC2-CUL5-associated p130 is related to the ROC1-CUL1-associated p130 (FIG. 3A, lane 7) and the functional roles these proteins may play in cullin-ROC complexes have not been determined. Cullin 2, 3 and 4 immunocomplexes, when precipitated from cells co-transfected with ROC2, but not APC11, contained a cellular protein of approximately 17 kda. The presence of this 17 kda polypeptide was not evident in either CUL1 or CUL5 immunocomplexes which contained little ROC2, suggesting that its association with cullin 2-4 is correlated with, and may actually be dependent on or is promoted by, the association of cullins with ROC2.

EXAMPLE 11

ROC1 and ROC2 do not Interact with APC2

APC11 was co-purified with another APC subunit, APC2, which contains limited sequence similarity to cullins (Zachariae et al., 1998; Yu et al., 1998a, supra). When tested by the two-hybrid assay, APC11, but not ROC1 nor ROC2, interacted with mouse APC2 in yeast cells (FIG. 4E). To assess the interaction between APC2 and these three closely related RING finger proteins in mammalian cells, HeLa cells were transfected with plasmids directing the expression of myc-epitope tagged APC2 with either HA-epitope tagged ROC1, ROC2 or APC11, and determined their respective bindings in vivo. Consistent with the yeast two-hybrid assay, APC2 and APC11 were reciprocally detected in APC11 and APC2 immunocomplexes, respectively (data not shown). Weak binding was detected between ectopically expressed ROC1 and APC2, but ROC2, even when overproduced, was not seen to interact with APC2 (data not shown).

EXAMPLE 12

Decrease of ROC1p Protein Causes a cdc53-, cdc34- and cdc4-Like Phenotype

The yeast genome contains a single ROC gene, Sc-ROC1 (ORF YOL133w), that shares 67% sequence identity with human ROC1 (FIG. 2B), providing a simpler and more genetically facile system to determine the in vivo function of ROC family proteins. The consequence of deleting the ScROC1 gene by replacing it with a kanamycin resistance module was determined by PCR homologous recombination. One copy of ScROC1 was replaced in a diploid, and the heterozygous yeast was subjected to sporulation and tetrad dissection (FIG. 5A). A 2:2 segregation was observed in 19 of 20 tetrads dissected on complete medium, and all of the viable colonies were kanamycin sensitive when replica plated onto selective medium (data not shown). Upon microscopic inspection of the inviable spores, germination and a limited number of cell divisions to form microcolonies were observed reflecting a "maternal" supply of ROC1p. Hence, ScROC1 appears to be an essential gene for yeast viability.

A conditional yeast strain in which ScROC1 was under the control of the galactose-inducible, glucose-repressible GAL1 promoter was created. An HA3 tag was fused in-frame with the ScROC1 gene to monitor the level of ROC1 protein expression. Transformants were sporulated and dissected (2:2 segregation was observed), and haploid yeast containing GAL-HA3-ScROC1 were isolated and verified by PCR analysis (data not shown) and protein expression (FIG. 5C). High levels of expression of HA3-ROC1p (FIG. 5B) or untagged ROC1p (data not shown) from the GAL1 promoter had no detectable effect on yeast growth. Repression of ScROC1 expression after switching to glucose resulted in a rapid decrease of ROC1p protein (FIG. 5C), suggesting that overexpressed ROC1p is an unstable protein with a short half life ($\sim t_{1/2} < 20$ minutes). Prolonged culturing of yeast cells in the presence of glucose, however, did not completely remove all of the ROC1 protein. A barely detectable amount of ROC1p was expressed for up to 24 hours when cultured in the presence of glucose, indicating that ROC1p may be continually expressed at a low level probably as the result of leakiness of the GAL1 promoter (FIG. 5C). Decrease of ScROC1 expression caused the yeast to begin exhibiting a mutant phenotype at nine hours and resulted in the accumulation of a multiply elongated budded yeast population containing a single nucleus by 24 hours (FIG. 5B).

The ROC1p depletion-induced phenotype is indistinguishable from those caused by temperature sensitive mutations in the CDC53, CDC4 and CDC34 genes (Mathias et al., 1996, supra). This result suggests that the ScROC1 gene is involved in the same pathway as these genes in controlling the ubiquitin-mediated proteolysis of proteins during the G1 phase of the cell cycle such as CDK inhibitor p40Sic1p. To provide evidence supporting this conclusion, it was determined whether the yeast ROC/APC11 family, like their human homologues, could directly interact with the yeast cullin/CDC53 family by the yeast-two-hybrid system. The yeast genome contains four cullin members, CDC53, CUL-B (ORF YGR003w), CUL-C (ORF YJL047c) and APC2. Each gene was fused in-frame with the Gal4 DNA binding domain and co-transformed with ScROC1 or ScAPC11 fused in-frame with the GAL4 activation domain. ScAPC2 was self-activating as a bait and was fused in-framed with the GAL4 activation domain and tested with ScROC1 fused in-frame with the DNA binding domain. ScROC1 interacted with all four yeast cullin genes including the most distantly related APC2 as determined by the activation of histidine reporter gene. In contrast, ScAPC11 only interacted weakly with CUL-C, but not CDC53 or CUL-B (FIG. 5D). Interaction of ScAPC11 with ScAPC2 could not be tested because both are self-activating as baits. Hence, like human ROC proteins, yeast ROC1 also commonly interacts with all members of cullin family proteins.

EXAMPLE 13

Functional Rescue of ROC1p Deficiency

Taking advantage of conditional phenotype induced by the depletion of ROC1p, the functional conservation and specificity of the ROC family proteins was determined. The multi-budded phenotype incurred by ROC1p depletion can be completely rescued by the expression of yeast ROC1, but not vector control (FIG. 5E), confirming that the level of ROC1p was the rate limiting factor causing the multi-budded phenotype. Ectopic expression of both human ROC1 and ROC2 also rescued the phenotype of ScROC1p depletion, but less efficiently than yeast ROC1 as evidenced by a small fraction of cells still exhibiting the phenotype. This indicates an evolutionary conservation of the ROC gene family and provides in vivo evidence supporting a function of human ROC1 in ubiquitin-mediated proteolysis. Ectopic expression of yeast APC11, on the other hand, did not rescue the phenotype caused by the decreased level of ROC1p (FIG. 5E), demonstrating a functional specificity between members of the ROC/APC11 family.

EXAMPLE 14

ROC1p is Required for SIC1p Degradation

A determination as to whether ScROC1 plays a role in regulating protein degradation was based on the phenotypic similarity between ROC1p depleted and cdc53 mutant cells and the interaction of ScROC1 with CDC53. A critical substrate of the CDC53 pathway is the G1 CDK inhibitor, p40Sic1p, which is targeted for ubiquitin mediated degradation by the yeast SCF (Skowyra et al., 1997; Feldman et al., 1997, supra). To determine whether Sic1p was stabilized in yeast depleted of ScROC1p, a yeast strain was created by PCR homologous recombination in which the SIC1 gene in the GAL-HA3-ScROC1 yeast was epitope tagged with HA3. Yeast cells grown in a low concentration of galactose (0.05% plus 2% raffinose), expressing a reduced level of ROC1p but still exhibiting a wild type phenotype, were switched to glucose media for different lengths of time to deplete the expression of ROC1p. Appearance of the multiple budded phenotype was confirmed by microscopic examination. Total cells lysates were prepared from samples collected from each time point and subjected to western analysis. The ROC1p protein was depleted and became almost undetectable after culturing in glucose media at the 9 hour point (data not shown). Closely correlated with the appearance of multiple elongated buds, Sic1 protein accumulated after 14 hours of culturing in glucose and was sustained at a high level throughout the experimental period (FIG. 5F). An anti-actin antibody was used to confirm the equal loading of proteins from different time points (FIG. 5F). These results provide in vivo evidence that ROC1 functions in ubiquitin-mediated proteolysis.

EXAMPLE 15

ROC1 is a Critical Subunit of Cullin Ubiquitin Ligase Activity

CDC53, the closest yeast homologue of human CUL1, assembles into a functional E3 ubiquitin ligase complex in insect cells with E2 CDC34, SKP1 and an F box protein (SCF complex) to catalyze ubiquitination of phosphorylated substrates (Skowyra et al., 1997; Feldman et al., 1997, supra). Protein complexes containing human CUL1, SKP 1 and SKP2 assembled in insect cells, however, were found to contain little ubiquitin ligase activity, but became active after incubating with HeLa cell lysate (Lyapina et al., 1998, supra), raising the possibility that an additional rate limiting component(s) is required for cullin-dependent ubiquitin ligase activity. To determine whether ROC1 may function biochemically as a subunit of ubiquitin ligase activity, the ubiquitin ligation activity of the ROC1 and CUL1 immunocomplexes was analyzed. 293T cells were transiently transfected with plasmid DNA expressing HA epitope tagged ROC1 (HA-ROC1) and cullin 1 and ROC1-CUL1 complex was recovered by immunoprecipitation using anti-HA antibody. To facilitate the recovery of functional ROC1- and cullin 1-associated ubiquitin ligase complex, the F-box protein SKP2, which has been previously demonstrated to interact with CUL1, was included in the transfection. SKP1, which mediates the binding of CUL1 with SKP2, is expressed at high level in the cell and was not included in the transfection. The ubiquitin ligase activity of ROC1 and CUL1 was measured by incubating the HA-ROC1-CUL1 immunocomplex immobilized on protein A agarose beads with purified human E1, mouse E2 CDC34, ATP and $^{32}$P-labeled ubiquitin (Ub). After incubation, the reactions were terminated by boiling the samples in the presence of SDS and reducing agent and mixtures were resolved by SDS-PAGE, followed by autoradiography. An evident, time-course dependent ubiquitin ligation, as visualized by the incorporation of $^{32}$P-Ub into covalently linked high molecular weight smear characteristic of ubiquitinated proteins, was detected when both E1 and E2 CDC34 were added to the HA-ROC1/CUL1/SKP2 immunocomplexes (lane 1, lanes 4 to 9, FIG. 6A), but not when either E1 (lane 2) or E2 (lane 3) was omitted, indicating an E1 and E2 dependent-ubiquitin ligation. As a control, anti-HA precipitate derived from cells transfected without a HA-tagged protein exhibited only E1- or E2-linked mono-ubiquitin conjugates (lanes 5 and 8, FIG. 6B). The observed protein ladder reflects an increment of a single 32P-Ub (~12 kDa in the form of a recombinant protein), a characteristic of ubiquitination reaction. The treatment of the reaction mixture with DTT, SDS and boiling significantly reduced, but cannot completely abolish the Ub-E1 (marked as 32P-Ub-E1, FIG. 6) and Ub-CDC34 (marked as 32P-Ub-CDC34) conjugates. No exogenous substrate protein was added to the reaction. Accumulation of high molecular weight ubiquitinated proteins could therefore be resulted from either the ubiquitination of a SKP2-targeted substrate(s) co-precipitated with the HA-ROC1 complex or a ligation of ubiquitin proteins. A careful examination of molecular weight increment from the ubiquitination reaction indicates that the ROC1-CUL1 complex can catalyze ubiquitin ligation independent of a substrate, and most, if not all high molecular weight masses correspond to polyubiquitin chains consisting of a series of ubiquitin molecules without an attached substrate (data not shown).

To determine the contribution of individual proteins to the ubiquitin ligase activity in the HA-ROC1 immunocomplex, a series of "drop-out" transfections was performed. Omission of SKP2, an F-box protein that presumably brings substrate protein(s) to CUL1, only slightly reduced the ubiquitin ligase activity (comparing lanes 2 and 3, FIG. 6B). Such a non-essential role of transfected SKP2 to the ubiquitin ligase activity of the HA-ROC1 complex may be due in part to the presence of endogenous SKP2 in 293 cells (Zhang, H., et al., (1995) *Cell* 82, 915-925), or indicating a substrate-independent ligation of ubiquitin molecules. Omission of CUL1, however, severely reduced the ubiquitin ligase activity of the ROC1 immunocomplex (lane 4). Reciprocally, omission of ROC1 from the CUL1 complex, like the omission of CUL1 from ROC1 complex, also significantly reduced ubiquitin ligase activity (comparing lanes 6 and 7). There was a low level of ligase activity in the CUL1 immunocomplex without co-transfection with ROC1, likely resulted from the endogenous ROC1 protein. These results indicate an inter-dependency of ROC1- and CUL1-associated ubiquitin ligase activity upon the expression of both proteins, suggesting that ROC1 and CUL1 act as integral parts of an E3 ubiquitin ligase.

EXAMPLE 16

In vivo Ubiquitin Ligase Activity of ROC1 and CUL1

To directly demonstrate a ROC1 associated ubiquitin ligase activity in vivo, ROC1 and CUL1 complexes from either 293T or HeLa cells were immunoprecipitated using affinity purified antibody specific to either protein and assayed for their ability to catalyze ubiquitin ligation (FIG. 6C). Like the HA-ROC1 immunocomplex precipitated from transfected cells, the ROC1 immunocomplex derived from both HeLa (lane 3) and 293T cells (lane 7) actively catalyzed the incorporation of $^{32}$P-labeled ubiquitin into high molecular weights in an E1 (lane 1) and E2 CDC34 (lane 2) dependent manner. Similarly, the CUL1 complex also exhibited a high level of ubiquitin ligase activity (lane 6). In contrast, the anti-APC11 complex exhibited only background levels of ligase activity when similarly incubated with E1 and E2 CDC34 (lane 5). It has this been determined that the anti-APC11 antibody is capable of precipitating APC11 as well as a number of additional cellular proteins, likely corresponding to other components of the APC complex (data not shown). These results, together with in vitro biochemical analysis demonstrating the catalytic role of the CUL1-ROC1 dimeric complex (Tan et al., accompanying paper), indicate that ROC1 is an essential subunit of cullin associated ubiquitin ligase.

EXAMPLE 17

Summation of Experimental Results

Four lines of evidence provided herein demonstrate that the ROC family proteins function as essential subunits of cullin ubiquitin ligases. First, both ROC1 and ROC2 interact directly with all five mammalian cullins that we have examined as determined by several different assays both in vitro and in vivo (FIGS. 1 and 3). Conventional biochemical purification has further identified ROC1 as a stoichiometrically associated subunit of CUL1 ubiquitin ligase activity (Tan et al., accompanying paper). Further underscoring the generality of this binary interaction is the parallel association in the APC E3 ligase between a cullin-related protein, APC2, and a ROC homologous protein, APC11 (FIG. 4). Among more than a dozen subunits identified, ROC/APC11 and cullin/APC2 are the only two proteins common between the APC and the SCF complexes.

Second, the examples set forth above demonstrate that ROC1 is essential for cullin function in vivo. Yeast ROC1 is an essential gene whose depletion results in a multiple elongated bud phenotype indistinguishable from that caused by cdc53, cdc34 and cdc4 mutations and results in accumulation of the CDK inhibitor Sic1 as in cdc53, cdc34 and cdc4 mutants. Similarly, ROC-related APC11 has been shown to be an essential subunit for APC function. Loss of APC11 function in yeast resulted in accumulation of APC substrates and caused metaphase arrest (Zachariae et al., 1998, supra).

Third, the examples above illustrate that ROC1 is an essential subunit of cullin ubiquitin ligase. ROC1 and cullin 1 immunocomplexes precipitated from in vivo catalyze ligation of ubiquitins to form polyubiquitin chains. Omission of ROC1 dramatically reduced ubiquitin ligase activity from the CUL1 immunocomplex (FIG. 6).

Finally, an in vitro ROC1 and CUL1 ubiquitin ligase activity that is specifically dependent on E1 and E2 has been reconstructed (Tan et al., accompanying paper).

One ramification of the findings set forth herein is that APC11 (ROC1 homologue) and APC2 (homologous to cullins) is the ligase in the APC. The extensive studies on ubiquitin-mediated proteolysis during the mitotic phase of the cell cycle have identified the APC as the single major E3 ubiquitin ligase required to degrade most mitotic regulatory proteins. Recently, yeast CDC53 has been identified as a major E3 ligase activity regulating S phase entry. Though the in vivo function of most cullins are yet to be determined, some may well perform other functions unrelated to cell cycle control. Although the ubiquitin ligase core of both APC and SCF complexes share structural similarities, one contains APC11 and APC2, the other involves CUL1 and ROC1, the two ligases exhibit an evident specificity. While both ROC proteins commonly interact with all cullins, APC11 specifically interacts with APC2. Functional support to this specificity comes from the finding that while both human ROC1 and ROC2 are capable of functionally rescuing the phenotype caused by the depletion of yeast ROC1, yeast APC11 can not (FTG. 5). Hence, ROC-cullin and APC11-APC2 function separately during interphase and mitosis, respectively. Furthermore, there exist two distinct ROC proteins in higher eukaryotes, both capable of directly interacting with all members of the cullin family. Their combinatorial interactions with different cullins point to a potentially large number of ubiquitin ligases, and each may be involved in a specific cellular pathway as in the case of the SCF and APC complexes, perhaps reflecting the complexity of interphase regulation.

The foregoing is illustrative of the present invention and is not to be construed as limiting thereof. The invention is defined by the following claims, with equivalents of the claims to be included therein.

The invention claimed is:

1. An isolated or recombinant RING finger protein that interacts with cullin proteins encoded by a polynucleotide, said polynucleotide selected from the group consisting of:
   (a) DNA having the nucleotide sequence of SEQ ID NO:3; and
   (b) a nucleotide sequence encoding the amino acid sequence of SEQ ID NO:4.

2. An isolated protein comprising the amino acid sequence of SEQ ID NO:4.

* * * * *